(12) United States Patent
Gascoyne et al.

(10) Patent No.: US 6,866,762 B2
(45) Date of Patent: Mar. 15, 2005

(54) DIELECTRIC GATE AND METHODS FOR FLUID INJECTION AND CONTROL

(75) Inventors: Peter Gascoyne, Bellaire, TX (US); Jon Schwartz, Sugar Land, TX (US); Jody V. Vykoukal, Houston, TX (US); Frederick F. Becker, Houston, TX (US)

(73) Assignee: Board of Regents, University of Texas System, Austin, TX (US)

( * ) Notice: Subject to any disclaimer, the term of this patent is extended or adjusted under 35 U.S.C. 154(b) by 206 days.

(21) Appl. No.: 10/028,945

(22) Filed: Dec. 20, 2001

(65) Prior Publication Data

US 2003/0121788 A1 Jul. 3, 2003

(51) Int. Cl.[7] .................... G01N 27/447; G01N 27/453
(52) U.S. Cl. ........................... 204/547; 204/643
(58) Field of Search ................................ 204/547, 643

(56) References Cited

U.S. PATENT DOCUMENTS

| | | | |
|---|---|---|---|
| 4,333,086 A | 6/1982 | Ebi | 346/140 |
| 4,390,403 A | 6/1983 | Batchelder | 204/180 |
| 5,126,022 A | 6/1992 | Soane et al. | 204/180.1 |
| 5,344,535 A | 9/1994 | Betts et al. | 204/183.1 |
| 5,454,472 A | 10/1995 | Benecke et al. | 209/127.1 |
| 5,486,337 A * | 1/1996 | Ohkawa | 422/100 |
| 5,569,367 A | 10/1996 | Betts et al. | 204/547 |
| 5,571,401 A | 11/1996 | Lewis et al. | 205/787 |
| 5,593,290 A | 1/1997 | Greisch et al. | 417/478 |
| 5,632,957 A | 5/1997 | Heller et al. | 422/68.1 |
| 5,653,859 A | 8/1997 | Parton et al. | 204/450 |
| 5,683,569 A | 11/1997 | Chung et al. | 205/775 |
| 5,795,457 A | 8/1998 | Pethig et al. | 204/547 |
| 5,814,200 A | 9/1998 | Pethig et al. | 204/547 |
| 5,858,192 A | 1/1999 | Becker et al. | 204/547 |
| 5,888,370 A | 3/1999 | Becker et al. | 204/547 |
| 5,965,452 A | 10/1999 | Kovacs | 436/149 |
| 5,993,630 A | 11/1999 | Becker et al. | 204/547 |
| 5,993,631 A | 11/1999 | Parton et al. | 204/547 |
| 5,993,632 A | 11/1999 | Becker et al. | 204/547 |
| 6,010,616 A | 1/2000 | Lewis et al. | 205/787 |

(List continued on next page.)

FOREIGN PATENT DOCUMENTS

| | | | |
|---|---|---|---|
| EP | 0513064 | 11/1992 | B03C/5/00 |
| EP | 0625267 | 11/1994 | G01N/33/48 |
| EP | 0680380 | 11/1995 | B03C/5/02 |
| EP | 0691891 | 1/1996 | B03C/5/00 |
| EP | 0898493 | 3/1999 | B01J/19/00 |
| WO | WO 93/16383 | 8/1993 | G01N/33/48 |
| WO | WO 94/16821 | 8/1994 | B03C/5/02 |
| WO | WO 97/34689 | 9/1997 | B01J/19/00 |
| WO | WO 99/36176 | 7/1999 | B01L/3/02 |
| WO | WO 99/62622 | 12/1999 | |
| WO | WO 00/47322 | 8/2000 | B01L/30/02 |
| WO | WO 00/69565 | 11/2000 | B03C/5/02 |

OTHER PUBLICATIONS

Jones et al. "Dielectrophoretic liquid actuation and nano-droplet formation," Journal of applied Physics, vol. 89, No. 2, Jan. 15, 2001, pp. 1441–1448.*

Derwent abstract of Gerisch et al. (DD 250661 A).*

Masao Washizu ( "Electrostatic Actuation of Liquid Droplets for Microreactor applications," IEEE Transactions on Industry Applications, vol. 34, No. 4, Jul./Aug. 1998, pp. 732–737).*

(List continued on next page.)

*Primary Examiner*—Alex Noguerola
(74) *Attorney, Agent, or Firm*—Fulbright & Jaworski LLP

(57) ABSTRACT

A dielectric gate and related systems and methods for controlling fluid flow. A dielectric gate includes one or more electrodes coupled between an inlet fluid pathway and an outlet fluid pathway. The electrodes are configured to draw fluid from the inlet fluid pathway to the outlet fluid pathway in a precise manner by using dielectric forces arising from electrical signals applied to the electrodes.

28 Claims, 19 Drawing Sheets

U.S. PATENT DOCUMENTS

| | | | |
|---|---|---|---|
| 6,017,696 A | 1/2000 | Heller | 435/6 |
| 6,024,925 A | 2/2000 | Little et al. | 422/100 |
| 6,071,394 A * | 6/2000 | Cheng et al. | 204/547 |
| 6,090,251 A | 7/2000 | Sundberg et al. | 204/453 |
| 6,093,308 A | 7/2000 | Lewis et al. | 205/787 |
| 6,099,803 A | 8/2000 | Ackley et al. | 422/68.1 |
| 6,113,768 A | 9/2000 | Fuhr et al. | 204/643 |
| 6,129,828 A | 10/2000 | Sheldon, III et al. | 204/518 |
| 6,130,098 A | 10/2000 | Handique et al. | 436/180 |
| 6,159,188 A | 12/2000 | Laibovitz et al. | 604/294 |
| 6,165,417 A | 12/2000 | Swierkowski | 422/100 |
| 6,221,653 B1 | 4/2001 | Caren et al. | 435/287.2 |
| 6,224,745 B1 | 5/2001 | Baltruschat | 205/775 |
| 6,225,059 B1 | 5/2001 | Ackley et al. | 435/6 |
| 6,287,832 B1 | 9/2001 | Becker et al. | 435/173.9 |
| 6,294,063 B1 | 9/2001 | Becker et al. | 204/450 |
| 6,565,727 B1 * | 5/2003 | Shenderov | 204/600 |

OTHER PUBLICATIONS

"Bangor biochip heads for California," EPSRC Home Page: http://www.epsrc.ac.uk/documents/about_epsrc/corporate_publi.../bangor.ht, article printed on Dec. 26, 2000.

"Diagnostic dielectrophoresis–on–a–chip," Science/Technology, 77(8):32, 1999. Article printed from http://pubs.acs.org/hotartcl/cenear/99022/7708scitobox2.html on Dec. 26, 2000.

Allsopp et al., "Impedance technique for measuring dielectrophoretic collection of microbiological particles," J. Phys. D: Appl. Phys., 32:1066–1074, 1999.

Balachandran et al., "Electrostatic atomization of conducting liquids using AC superimposed on DC fields," IEEE Transactions on Industry Applications, 30(4):850–854, 1994.

Cheng et al., "Preparation and hybridization analysis of DNA/RNA form E. coli on microfabricated biolectronic chips," Nature Biotechnology, 16:541–546, 1998.

El–Kishky and Gorur, "Electric field and energy computation on wet insulating surfaces," IEEE Transaction on Dielectrics and Electrical Insulation, 3(4):587–593, 1996.

El–Kishky and Gorur, "Electric field computation on an insulating surface with discrete water droplets," IEEE Transactions on Dielectrics and Electrical Insulation, 3(3):450–456, 1996.

Fuller et al., "Microfabricated multi–frequency particle impedance characterization system," Micro Total Analysis System, van den Berg et al., 265–268, 2000.

Galicki et al., "Electrohydrodynamic atomization of dielectric fluids," Conference on Electrical Insulation and Dielectric Phenomena, IEEE Annual Report, 365–368, 1996.

Gawad et al., "Impedance spectroscopy cell anaylsis in microchannels," Micro Total Analysis Systems, 253–255, 2001.

Gawad et al., "Micronarcined impedance spectroscopy flow cytometer for cell analysis and particle sizing," Lab on a Chip, 1:76–82, 2001.

He et al., "Droplet charge–to–mass ratio measurement in an EHD liquid–liquid extraction system," IEEE Transactions on Industry Applications, 32(1):146–154, 1996, Jan./Feb.

Higashiyama et al., "Behavior of water droplets located on a hydrophobic insulating plate under DC field," IEEE, 1808–1813, 1998.

Hoffman and Britt, "Flow–system measurement of a cell impedance properties," J. Histochemistry and Cytochemistry, 27:234–240, 1979.

Hoffman et al., "Flow cytometric electronic direct current volume and radiofrequency impedance measurments of single cells and particles," Cytometry, 1:377–384, 1981.

Hosokawa et al., "Handling of picoliter liquid samples in a Poly(dimethylsiloxane)–based microfluidic device," Anal. Chem., 71:4781–4785, 1999.

Huneiti et al., "Harmonic spraying of conducting liquids employing AC–DC electric fields," IEEE Transactions on Industry Applications, 34(2):279–285, 1998.

Jones, Electromechanics of Particles, Cambridge University Press, Cambridge, Chapter 3:34–82, 1995.

Kashyap and Gratzl, "Electrochemistry in microscopic domains. 1. The electrochemical cell and its voltammetric and amperometric response," Anal Chem., 70:1468–1476, 1998.

Kloes and Koenig, "Basic investigation of the performance of droplets on electrically stressed polymer surfaces," Conference on Electrical Insulation and Dielectric Phenomena, IEEE Annual Report, 374–377, 1997.

Lee and Kim, "Liquid micromotor driven by continuous electrowetting," IEEE, 538–543,1998.

Metwally, "Electrostatic charging and modeling of aqueous sprays and fission of droplets," Conference on Electrical Insulation and Dielectric Phenomena, IEEE Annual Report, 117–120, 1996.

Mizuno et al., "Behavior of water droplets on silicone rubber sheet under AC voltage application," IEEE, 96–99, 1998.

Moesner et al., "Electrostatic devices for particle microhandling," IEEE Transactions on Industry Applications, 35(3):530–536, 1999.

Sathuvalli and Bayazitoglu, "The lorentz forces on an electrically conducting sphere in an alternating magnetic field," IEEE Transactions on Magnetics, 32(2):386–399, 1996.

Sato et al., "Experimental investigation of droplet formation mechanisms by electrostatic dispersion in a liquid–liquid system," IEEE Transactions on Industry Applications, 33(6):1527–1534, 1997.

Sato et al., "Production of oil/water type uniformly sized droplets using a convergent AC elctric field," IEEE Transactions on Industry Applications, 32(1):138–145, 1996.

Wang et al., "A theoretical method of electrical field analysis for dielectrophoretic electrode arrays using Green's theorum," J. Phys. D: Appl. Phys., 29:1649–1660, 1996.

Wang et al., "Separation of polystyrene microbeads using dielectrophoretic/gravitational field–flow–fractionation," Biophysical Journal, 74:2689–2701, 1998.

Washizu, "Electrostatic actuation of liquid droplets for microreactor applications," IEEE Transactions on Industry Applications, 34(4):732–737, 1998.

Co Pending U.S. Appl. No. 09/833,110, filed Jun. 14, 2001, Peter Gascoyne et al.

* cited by examiner ified
DIELECTRIC GATE AND METHODS FOR FLUID INJECTION AND CONTROL The government may own rights to aspects of the present invention pursuant to grant number N66001-97-C-8608 modification 3 from the Defense Advanced Research Projects Agency. The government may also own rights to aspects of the present invention pursuant to grant no. DAAD19-00-1-0515 from the Army Research Office.

BACKGROUND OF THE INVENTION

Other patents and application that may be used in conjunction with the current disclosure include U.S. Pat. No. 5,858,192, entitled "Method and apparatus for manipulation using spiral electrodes," filed Oct. 18, 1996 and issued Jan. 12, 1999; U.S. Pat. No. 5,888,370 entitled "Method and apparatus for fractionation using generalized dielectrophoresis and field flow fractionation," filed Feb. 23, 1996 and issued Mar. 30, 1999; U.S. Pat. No. 5,993,630 entitled "Method and apparatus for fractionation using conventional dielectrophoresis and field flow fractionation," filed Jan. 31, 1996 and issued Nov. 30, 1999; U.S. Pat. No. 5,993,632 entitled "Method and apparatus for fractionation using generalized dielectrophoresis and field flow fractionation," filed Feb. 1, 1999 and issued Nov. 30, 1999; U.S. patent application Ser. No. 09/395,890 entitled "Method and apparatus for fractionation using generalized dielectrophoresis and field flow fractionation," filed Sep. 14, 1999; U.S. patent application Ser. No. 09/883,109 entitled "Apparatus and method for fluid injection," filed Jun. 14, 2001; U.S. patent application Ser. No. 09/882,805 entitled "Method and apparatus for combined magnetophoretic and dielectrophoretic manipulation of analyte mixtures," filed Jun. 14, 2001; U.S. patent application Ser. No. 09/883,112 entitled "Dielectrically-engineered microparticles," filed Jun. 14, 2001; U.S. patent application Ser. No. 09/883,110 entitled "Systems and methods for cell subpopulation analysis," filed Jun. 14, 2001; and U.S. patent application Ser. No. 10/005,373, now U.S. Pat. No. 6,703,819 entitled "Particle Impedance Sensor," by Gascoyne et al. filed Dec. 3, 2001 and issued Mar. 9, 2004; each of which are herein expressly incorporated by reference.

Yet another application that may be used in conjunction with the teachings of the current invention include those described in "Micromachined impedance spectroscopy flow cytometer of cell analysis and particle sizing," Lab on a Chip, vol. 1, pp. 76–82 (2001), which is incorporated by reference.

1. Field of the Invention

The present invention relates generally to fluidic processing and, more particularly, to methods and apparatuses to controllably inject fluid packets onto a surface. Even more particularly, the present invention relates to methods and apparatuses for programmably injecting fluid packets onto a surface using dielectrophoretic forces, including uses of dielectric gates.

2. Description of Related Art

Chemical protocols often involve a number of processing steps including metering, mixing, transporting, division, and other manipulation of fluids. For example, fluids are often prepared in test tubes, metered out using pipettes, transported into different test tubes, and mixed with other fluids to promote one or more reactions. During such procedures, reagents, intermediates, and/or final reaction products may be monitored, measured, or sensed in analytical apparatus. Microfluidic processing generally involves such processing and monitoring using minute quantities of fluid. Microfluidic processing finds applications in vast fields of study and industry including, for instance, diagnostic medicine, environmental testing, agriculture, chemical and biological warfare detection, space medicine, molecular biology, chemistry, biochemistry, food science, clinical studies, and pharmaceutical pursuits.

Current approaches directed at fluidic processing exhibit several shortcomings. One current approach to microfluidic processing utilizes a number of microfluidic channels that are configured with microvalves, pumps, connectors, mixers, and detectors. While devices using micro-scale implementations of these traditional approaches may exhibit at least a degree of utility, vast room for improvement remains. For instance, current microfluidic devices lack flexibility for they rely upon a fixed pathway of microchannels. With fixed pathways, devices are limited in the number and type of tasks they may perform. Also, using fixed pathways makes many types of metering, transport, and manipulation difficult. With traditional devices, it is difficult to partition one type of sample from another within a channel.

Other current approaches involve electrical properties of materials. In particular, certain electrical properties of materials have been employed to perform a limited number of fluidic processing tasks. For example, dielectrophoresis has been utilized to aid in the characterization and separation of particles, including biological cells. An example of such a device is described in U.S. Pat. No. 5,344,535 to Betts, incorporated herein by reference. Betts establishes dielectrophoretic collection rates and collection rate spectra for dielectrically polarizable particles in a suspension. Particle concentrations at a certain location downstream of an electrode structure are measured using a light source and a light detector, which measures the increased or decreased absorption or scattering of the light which, in turn, indicates an increase or decrease in the concentration of particles suspended in the fluid. Although useful for determining particle dielectrophoretic properties, such a system is limited in application. In particular, such a system does not allow for general fluidic processing involving various interactions, sometimes performed simultaneously, such as metering, mixing, fusing, transporting, division, and general manipulation of multiple reagents and reaction products.

Another example of using certain electrical properties for specific types of processing is disclosed in U.S. Pat. No. 5,632,957 to Heller et al., incorporated herein by reference. There, controlled hybridization may be achieved using a matrix or array of electronically addressable microlocations in conjunction with a permeation layer, an attachment region and a reservoir. An activated microlocation attracts charged binding entities towards an electrode. When the binding entity contacts the attachment layer, which is situated upon the permeation layer, the functionalized specific binding entity becomes covalently attached to the attachment layer. Although useful for specific tasks such as DNA hybridization, room for improvement remains. In particular, such a system, utilizing attachment sites for certain binding entities is designed for particular applications and not for general fluidic processing of a variety of fluids. More specifically, such a system is designed for use with charged binding entities that interact with attachment sites.

Another example of processing is disclosed in U.S. Pat. No. 5,126,022 to Soane et al., incorporated herein by reference. There, charged molecules may be moved through a medium that fills a trench in response to electric fields generated by electrodes. Although useful for tasks such as separation, room for improvement remains in that such devices are not well suited for performing a wide variety of fluidic processing interactions on a wide variety of different materials.

There are other examples of using dielectrophoresis for performing specific, limited fluidic processing tasks. U.S. Pat. No. 5,795,457 to Pethig and Burt, incorporated herein by reference, disclose a method for promoting reactions between particles suspended in liquid by applying two or more electrical fields of different frequencies to electrode arrays. While perhaps useful for facilitating certain interactions between many particles of different types, the method is not well suited for general fluidic processing. U.S. Pat. No. 4,390,403 to Batchelder, incorporated herein by reference, discloses a method and apparatus for manipulation of chemical species by dielectrophoretic forces. Although useful for inducing certain chemical reactions, its flexibility is limited, and it does not allow for general, programmable fluidic processing.

Although using a syringe, a micropipette, or the like allows for injection of material onto the surface, shortcomings remain. For instance, such an inlet does not always provide for systematic, controllable injection of material. In particular, using existing devices and techniques does not always ensure that a controllable, single drop is injected at a time. Rather, existing technology often results in the injection of one drop at one time, two drops together at another time, etc. Hence, the controllability and metering capabilities of existing technology is not completely adequate. Without controllable packet injection, the accuracy and repeatability of certain microfluidic processing tasks may suffer.

In light of the above, it would be advantageous to provide for technology in which metered packets of material could be systematically injected onto a surface in a reliable, repeatable manner. It would further be advantageous is the method of injection were automated so that processing could take place with little, or no operator intervention. Such advantages would potentially benefit all realms of microfluidic processing and/or any field in which a controllable manner of injecting packets of materials is desired.

Any problems or shortcomings enumerated in the foregoing are not intended to be exhaustive but rather are among many that tend to impair the effectiveness of previously known processing and fluid injection techniques. Other noteworthy problems may also exist; however, those presented above should be sufficient to demonstrated that apparatus and methods appearing in the art have not been altogether satisfactory and that a need exists for the techniques disclosed herein.

SUMMARY OF THE INVENTION

In one respect, this disclosure relates to a method for metered injection of a fluid packet. A vessel containing the packet is pressurized to a pressure less than or equal to a hold-off pressure. The packet is subjected to an extraction force to extract the packet from the vessel onto a surface.

In other respects, the extraction may include dielectrophoresis. It may also include magnetophoresis or any other suitable force. The extraction force may produced by an electrode, an electrode array or any other suitable apparatus. The extraction force may be produced from the reaction surface.

In other respects, the vessel may comprise a flow-through injector. The pressure may be between 0% and 95% of the holdoff pressure, or more preferably between 75% and 85% of the holdoff pressure. The size of the packet may be electronically controlled.

Another aspect of this disclosure includes removing the packet from the surface through an exit port. There may be two or more exit ports, and the exit ports may be coupled to a conventional fluidics device.

Yet another aspect of this disclosure comprises a method for metered injection of two or more fluid packets from two or more pressurized vessels. A switching pump may be used. The switching pump switches the extraction force between a first packet in a first pressurized vessel and a second packet in a second pressurized vessel.

In another respect, this disclosure relates to a method for metered injection of a fluid packet. A vessel containing the packet is pressurized to a pressure less than or equal to a hold off pressure, the packet including a first dielectric material. One or more electrodes coupled to a surface adjacent the vessel are energized, the surface including a fluid comprising a second dielectric material. The packet is subjected to an extraction force from the one or more electrodes to extract the packet from the vessel onto a surface.

In another respect, this disclosure relates to an apparatus for injecting a fluid packet onto a surface. The apparatus includes a vessel, a pressure manifold, a pressure reservoir, and a device capable of generating a programmable extraction force. The vessel is configured to contain the packet. The pressure manifold is coupled to the vessel. The pressure reservoir is coupled to the manifold and is configured to pressurize the vessel to a pressure less than or equal to a hold off pressure. The extraction force is configured to extract the packet from the vessel onto the surface. There may be two or more pressure reservoirs or the vessel may comprise a flow-through injector.

In yet another respect, this disclosure relates to an apparatus for moving a fluid packet, the apparatus comprising. The apparatus includes a vessel, a pressure manifold, a pressure reservoir, a device capable of generating a programmable extraction force and an exit port. The vessel is configured to contain the packet. The pressure manifold is coupled to the vessel. The pressure reservoir is coupled to the manifold and is configured to pressurize the vessel to a pressure less than or equal to a hold off pressure. The extraction force is configured to extract the packet from the vessel onto the surface. The exit port is coupled to the surface and configured to receive the packet. The exit port is preferably hydrophilic. There can be a plurality of exit ports. A conventional fluidics device may be coupled to the exit port.

The vessel may comprise a flow-through injector, and there may be two or more pressurized vessels. A switching pump may be used when there are more than one vessels or exit ports. The switching pump is configured to switch the extraction force between a first packet in a first pressurized vessel and a second packet in a second pressurized vessel.

In yet another respect, the present disclosure relates to a dielectric gate including one or more electrodes coupled between an inlet fluid pathway and an outlet fluid pathway. The one or more electrodes are configured to draw fluid from the inlet fluid pathway to the outlet fluid pathway using dielectric forces arising from electrical signals applied to the one or more electrodes. The inlet fluid pathway may include a tube or channel. The inlet fluid pathway may include hydrophilic or hydrophobic surface coatings configured to provide preferential fluid flow directions. The gate may also include a fluidic injector in operative relation to the inlet fluid pathway, and the fluidic injector may include a hydrophilic or hydrophobic coating.

In yet another respect, the present disclosure relates to a dielectric gate including an inlet fluid pathway, one or more electrodes, a hydrophobic patch, and an outlet fluid pathway. The one or more electrodes are in operative relation with the inlet fluid pathway. The hydrophobic patch is adjacent at least one of the electrodes. The outlet fluid pathway is in operative relation with at least one of the electrodes. The one or more electrodes are configured to draw fluid from the inlet fluid pathway to the outlet fluid pathway using dielectric forces arising from electrical signals applied to the one or more electrodes. The hydrophobic patch is configured to inhibit fluid flow from the inlet fluid pathway to the outlet fluid pathway in the absence of the electrical signals.

In yet another respect, the present disclosure relates to a system for fluid flow control, including a dielectric gate, a fluid reservoir, and a fluidic device. The dielectric gate includes an inlet and outlet fluid pathway. The fluid reservoir is coupled to the inlet fluid pathway of the dielectric gate, and the fluidic device is coupled to the outlet fluid pathway of the dielectric gate. The dielectric gate includes one or more electrodes configured to draw fluid from the fluid reservoir via the inlet fluid pathway to the fluidic device via the outlet fluid pathway using dielectric forces arising from electrical signals applied to the one or more electrodes. The dielectric gate may include a hydrophobic patch adjacent one or more of the electrodes and configured to inhibit fluid flow from the inlet fluid pathway to the outlet fluid pathway in the absence of the electrical signals. The system may also include an impedance sensor in operative relation to the dielectric gate, which is configured to count a number of droplets transferred from the inlet fluid pathway to outlet fluid pathway. The entire system may be incorporated onto a single chip. The fluidic device may include a capillary electrophoresis device, a polymerase chain reaction device, a dielectrophoresis field flow fractionation device, a programmable fluidic processor, or any other fluidic apparatus suitable to accept flow from one or more outlet fluid pathways.

In yet another respect, the present disclosure relates to a method for fluid flow control. Fluid is flowed from a fluid reservoir to an inlet fluid pathway. The fluid is drawn from the inlet fluid pathway to an outlet fluid pathway by dielectric forces arising from a dielectric gate, and the fluid is flowed from the outlet fluid pathway to a fluidic device. The method may also include inhibiting the flow of fluid from the inlet fluid pathway to the outlet fluid pathway using a hydrophobic patch coupled to at least a portion of the dielectric gate. The method may also include counting a number of droplets transferred from the inlet fluid pathway to outlet fluid pathway using an impedance in operative relation to the dielectric gate. The step of flowing fluid from the fluid reservoir to the inlet fluid pathway may involve flowing the fluid through one or more virtual channels defined by hydrophilic or hydrophobic surface coatings, which provide a preferential fluid flow direction. Likewise, the step of flowing the fluid from the outlet fluid pathway to the fluidic device may involve flowing the fluid through one or more virtual channels defined by hydrophilic or hydrophobic surface coatings, which provide a preferential fluid flow direction.

As used herein, "packet" refers to compartmentalized matter and may refer to a fluid packet, an encapsulated packet, and/or a solid packet. A fluid packet refers to one or more packets of liquids or gases. A fluid packet may refer to a packet or bubble of a liquid or gas. A fluid packet may refer to a packet of water, a packet of reagent, a packet of solvent, a packet of solution, a packet of sample, a particle or cell suspension, a packet of an intermediate product, a packet of a final reaction product, or a packet of any material. An example of a fluid packet is a packet of aqueous solution suspended in oil. An encapsulated packet refers to a packet enclosed by a layer of material. An encapsulated packet may refer to vesicle or other microcapsule of liquid or gas that may contain a reagent, a sample, a particle, a cell, an intermediate product, a final reaction product, or any material. The surface of an encapsulated packet may be coated with a reagent, a sample, a particle or cell, an intermediate product, a final reaction product, or any material. An example of an encapsulated packet is a lipid vesicle containing an aqueous solution of reagent suspended in water. A solid packet refers to a solid material that may contain, or be covered with a reagent, a sample, a particle or cell, an intermediate product, a final reaction product, or any material. An example of a solid packet is a latex microsphere with reagent bound to its surface suspended in an aqueous solution. Methods for producing packets as defined herein are known in the art. Packets may be made to vary greatly in size and shape, but in embodiments described herein, packets may have a diameter between about 100 nm and about 1 cm.

As used herein, a "conventional fluidics device" is one that contains channels and/or tubes for fluid flow. A "vessel" is defined herein as a container or conduit capable of containing fluids.

BRIEF DESCRIPTION OF THE DRAWINGS

The following drawings form part of the present specification and are included by way of example and not limitation to further demonstrate certain aspects of the present invention. The invention may be better understood by reference to one or more of these drawings, in combination with the detailed description of specific embodiments presented herein.

DESCRIPTION OF ILLUSTRATIVE EMBODIMENTS

Figure 1:
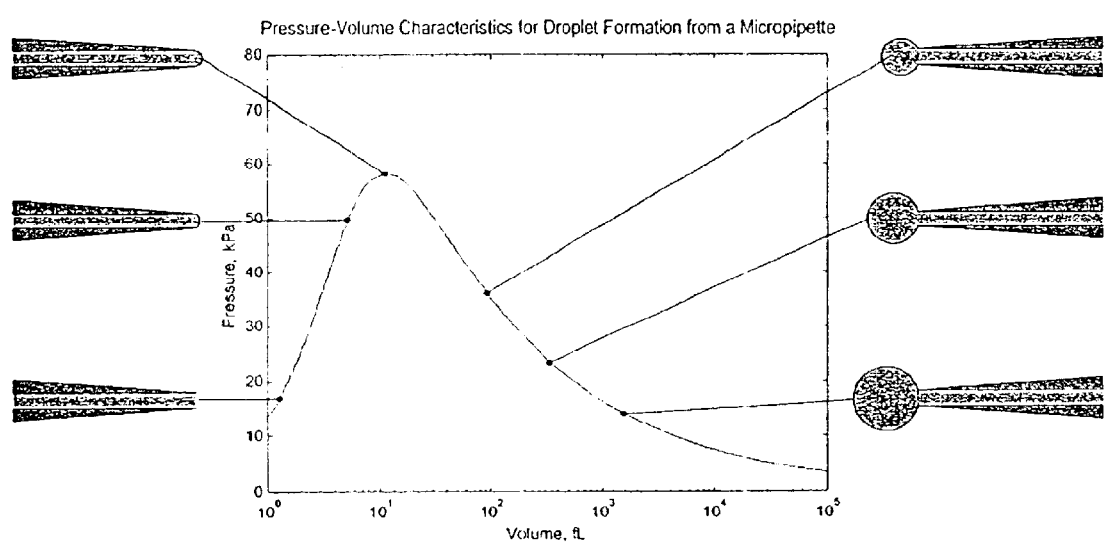
FIG. 1 is a graph and an illustration that demonstrates the pressure and volume characteristics for water packet formation from a 5 micron diameter micropipette according to embodiments of the present disclosure. In this figure, the peak pressure occurs when the radius of the packet is one-half the diameter of the tube orifice.

The presently disclosed methods and apparatuses provide many advantages. For instance, they permit for the high-resolution, metered injection of fluid packets that, in turn, allows for fluidic processing of minute quantities of samples and reagents. They permit automated fluid injection that may be programmed according to a particular fluidic processing application. They allow for the fluid packets of different volume to be created and injected in a highly controllable, consistent manner. The ability to create and inject such metered packets provides for the ability to perform accurate, automated microfluidic processing in a variety of different fields. The apparatuses described herein may be readily miniaturized (or made larger) to fit the needs of the user. Its processes may be automated or programmed, manual, or partially automated. The techniques disclosed herein may be used for many different types of microfluidic processing and protocols, and it may be used in processes that are operated in parallel mode, whereby multiple fluidic processing tasks and reactions are performed simultaneously within a single chamber. Areas that may benefit from this technology include, but are not limited to: blood and urine assays, pathogen detection, pollution monitoring, water monitoring, fertilizer analysis, the detection of chemical and biological warfare agents, food pathogen detection, quality control and blending, massively parallel molecular biological protocols, genetic engineering, oncogene detection, and pharmaceutical development and testing.

Because the present disclosure deals, in part, with the formation and injection of fluid packets, it is useful to begin the discussion with some theoretical underpinnings of the techniques disclosed herein.

Packet Volume-Pressure Characteristics.

To understand modes of operation of a packet injector that uses dielectrophoretic extraction forces, it is useful to first consider the pressure that must be applied to a fluid-filled tube in order to cause the formation of a fluid packet at the open end of tube. Here, the case is considered in which the diameter of the tube orifice is sufficiently small so that surface-energy effects cause the fluid to form a smooth front and that, initially, the applied pressure is low enough so that the fluid fills the tube flush with its end. As the pressure is increased, it is assumed that the shape of the emerging packet approximates a segment of a spherical surface. The pressure inside a packet is proportional to the interfacial tension γ at its surface and inversely proportional to its radius r, and is given by:

$$P = \frac{2\gamma}{r}.$$

Initially, when the packet is flush with the end of the tube, the effective radius is infinite, and so the pressure is equal to zero. As the fluid surface becomes more curved, the radius decreases. However, once the packet forms a hemisphere at the orifice of the tube, any further increase in volume again results in an increase in packet radius. As the packet continues to grow, its internal pressure decreases as r continues to increase. Thus, the minimum radius depends on the diameter of the orifice and this, in turn, determines the maximum pressure in the packet.

This effect is illustrated in FIG. 1, which shows, in the side panels, the appearance of fluid emerging from the tip of a micropipette and, on the graph, the corresponding pressure inside the packet during packet formation. It is apparent from FIG. 1 that if the fluid is pressurized to form a packet that is less than hemispherical, packet formation will proceed no further because additional pressure would be required to accomplish this. In this case, it may be said that packet formation is "held off". However, if the pressure is increased to the peak value, fluid will flow into the packet continuously because increasing the packet size above the hemispherical condition occurs easily as the internal packet pressure falls with increasing volume. The peak pressure is termed the "hold-off pressure," because until that pressure is reached, packet formation will not proceed.

In injector designs described herein, an injector tip may be connected to a fluid reservoir formed either by the bore of a tube or by a larger fluid container to which the other end of the bore is connected. Such a fluid reservoir may be pressurized to a pressure $P_f$ that may be provided by an external pressure source derived from any suitable source such as a gas pressure, a pump, a membrane under compression, an electroosmotic fluid pressure source, or any other device as is known in the art. The pressure value $P_f$ may be kept below the hold-off pressure for the injector so that packet formation is held-off as shown in the left hand panel of FIG. 1.

Dielectrically-Induced Forces on a Packet

In one embodiment, electrical forces may be used to influence the formation of packets like those described above. Because the electrical equations are geometry dependent, however, the theoretical discussion presented here is meant to be illustrative only and not limiting. Specifically, it illustrates the physical principles rather than providing specific equations applicable to all different geometrical arrangements. One having skill in the art will recognize that in any given embodiment, the exact form of the equations may differ somewhat from those presented here, but the physical principles governing packet injection will be similar, if not the same. Thus, having the benefit of the illustrative examples given herein, equations and solutions applicable to arbitrarily different arrangements will be readily apparent to those having skill in the art.

If a small sphere of a first dielectric material (which may include a solid, liquid or gas) is introduced into a second, dissimilar dielectric material to which an electrical field is applied, the energy of the combined system of dielectric materials will be changed, in comparison with the energy before the introduction occurred, as the result of the difference in the polarizabilities of the two dielectric materials. This energy change is proportional to W, which may be approximated as $$W = 2\pi \in_s r^3 f_{CM} \overline{E}^2$$

where $\overline{E}$ is the electrical field, $\in_s$ is the permittivity of the second dielectric material, r is the radius of the small sphere, and $\overline{E}$ is the applied electrical field. The term $f_{CM}$ is the so-called Clausius-Mossotti factor, known in the art, that expresses the polarizability of the sphere in terms of the differences between complex dielectric permittivities of the first material, $\in^*_f$, and that of the second material, $\in^*_s$, and, if the electrical field is not traveling through space, is given by $$f_{CM} = \text{Re}\left(\frac{\varepsilon^*_f - \varepsilon^*_s}{\varepsilon^*_f + 2\varepsilon^*_s}\right).$$

For the present discourse, assume that the first dielectric material is the fluid that is about to be injected from the end of a tube as shown in the left-hand panel of FIG. 1 and that the second material is an immiscible liquid or gas that surrounds the end of the tube and the emergent fluid. The second liquid or gas may be called the "suspending medium."

An applied electric field emanating from the end of the tube will tend to alter the pressure at the fluid-suspending medium interface, and this pressure change will in turn alter the volume of the packet according to FIG. 1. The pressure change may be estimated by determining the rate of change of electrical energy, W, with fluid radius, r. This is given by $$F_{dielectric} = \frac{\partial W}{\partial r} = 3\pi\varepsilon_s r^2 f_{CM} \overline{E}^2 + 2\pi\varepsilon_s r^3 f_{CM} \overline{E} \cdot \frac{\partial \overline{E}}{\partial r}.$$

The term $3\pi\varepsilon_s r^2 f_{CM}\overline{E}^2$ represents a force that results from the dielectric energy change associated with displacement of the suspending medium by the injected fluid. The term $$2\pi\varepsilon_s r^2 f_{CM} \overline{E} \cdot \frac{\partial \overline{E}}{\partial r}$$

is a dielectrophoretic term that acts on the fluid as the result of inhomogeneity in the electrical field. The effect of these two force contributions on the pressure in the fluid can be estimated by determining the corresponding pressure change, P, or force per unit area, that results at the fluid-suspending medium interface:

$$P = \frac{F_{dielectric}}{A_{fluid}} = \frac{F_{dielectric}}{4\pi r^2} = \frac{3}{4}\varepsilon_s f_{CM} \overline{E}^2 + \frac{1}{2}\varepsilon_s r f_{CM} \overline{E} \cdot \frac{\partial \overline{E}}{\partial r}$$

If it is assumed that the electrical field arises from a voltage V applied between the fluid in the tube and a second, pointed electrode positioned a distance d outside the tube and within the suspending medium, then, to illustrate the effects on packet pressure, the potential configuration can be approximated as being broadly similar to that produced by a source of strength V/2 and a sink of strength −V/2 of a vector field positioned at the origin and Z=d in the two dimensional complex plane, respectively. By superposition theory, the potential distribution in the z-plane is then $$V(z) = \frac{V}{2}[\log(z) - \log(z-d)].$$

Differentiating with respect to z the vector field and field gradient are obtained, respectively, as $$\overline{E}(z) = \left(\frac{Vd}{2}\right)\left(\frac{1}{z(d-z)}\right) \text{ and } \frac{\partial \overline{E}(z)}{\partial z} = -\left(\frac{Vd}{2}\right)\left(\frac{d-2z}{z^2(d-z)^2}\right).$$

Substituting these expressions into that for the pressure change at the fluid-suspending medium interface, the following equation is obtained:

$$P = \frac{\varepsilon_s}{2}\left(f_{CM}\left(\frac{Vd}{2}\right)\right)^2\left(\frac{1}{(z^2(d-z))^2}\right)\left\{\frac{3}{2} - \frac{r(d-2z)}{z(d-z)}\right\}.$$

The pressure induced electrically depends upon the square of the voltage V, implying not only that the direction of the applied voltage is unimportant but that alternating current (AC) fields may be used. In practice, the use of AC fields is very advantageous because fields of sufficiently high frequency may be coupled capacitively from electrodes insulated by a thin layer of dielectric material (such as Teflon or any other suitable insulating material) into chambers where fluid packet manipulations are to be carried out. In addition, the use of AC fields permits the frequency dependencies of the dielectric permittivity of the fluid, $\in^*_f$, of the suspending medium, and that of any matter within the fluid, to be exploited if desired. These frequency dependencies result in different behavior of the materials at different applied field frequencies and, under appropriate circumstances, may result in useful changes in the direction of dielectrophoretic forces as the frequency is varied.

To an approximation, the effect of the electrical field on packet formation at the tube outlet may be judged by examining the pressure properties along the x axis at the position z=r. Substituting this condition into the pressure equation in the early stages of packet formation when r is small compared to the distance d to the other electrode, the following approximate expression may be written:

$$P \approx \frac{\varepsilon_s}{2}\left(f_{CM}\left(\frac{V}{2r}\right)\right)^2\left\{\frac{3}{2} - 1\right\} = \frac{\varepsilon_s}{4}\left(f_{CM}\left(\frac{V}{2r}\right)\right)^2.$$

In this case, the pressure change at the fluid-suspending medium interface is dominated by the dielectric energy resulting from displacement of the suspending medium.

It should be stressed that this pressure change does not depend upon net charge on the packet, and this even further distinguishes this dielectric method from those that depend upon net electrostatic charging as a means for injection of packets or for forming particulates or aerosols. Indeed, when AC fields are used for dielectric injection, the presence of net charge does not alter the pressure induced by the applied AC field because the time-averaged magnitude of an AC field is zero. However, if desired, the dielectric method may be used to improve injection of charged packets. By applying a DC voltage component to the fluid in addition to an AC component, the injected packets will carry a charge that affects the injection characteristics.

The dielectrophoretic forces may be generated by an array of individual driving electrodes fabricated on an upper surface of a reaction surface. The driving electrode elements may be individually addressable with AC or DC electrical signals. Applying an appropriate signal to driving electrode sets up an electrical field that generates a dielectrophoretic force that acts upon a packet contained in an injection tip or vessel. Switching different signals to different electrodes sets up electrical field distributions within a fluidic device. This can be used for the injection of different packets from different injection tips into the device. Such electrical field distributions may be utilized to inject packets into a partitioning medium.

Dielectric Injection of Fluid Packets into Low-Dielectric Constant Liquids

In the case of water packets being injected into an immiscible, low-dielectric constant suspending medium, the water is much more polarizable than the suspending medium and $f_{CM}$ assumes a value very close to +1. In this case, the pressure in the packet is increased by the presence of the electrical field.

In a packet injection, V may have a value of about 180 Volts and, with a 5 micron tube diameter and an applied hydrostatic pressure of about 50 kPa (see the pressure-packet volume data for injection into bromododecane given in FIG. 1), then the pressure increment P arising from the voltage application is calculated to be about 18 kPa. The combined hydrodynamic and dielectric pressures on the fluid-suspending medium interface, therefore, total 50 kPa+18 kPa=68 kPa, which is well in excess of the hold off pressure for the orifice shown in FIG. 1. Therefore, fluid will flow from the tube into the packet and will allow a packet of large size to be formed. Once the packet volume exceeds 30 fl, the pressure needed to inflate the packet still further falls below 50 kPa (see FIG. 1) and the packet will continue to grow in size even if the electrical field is removed at that point.

However, if the field is maintained, the above pressure equations reveal that the sign of the dielectrophoretic pressure term will change when r>d/2, and the dielectrophoretic force will not only aid packet growth but will also provide a lateral force component directed towards the other electrode.

In general, packets will not remain perfectly spherical as assumed in the above derivations because they will conform to a shape in which the pressure at the fluid-suspending medium interface is equal everywhere at the fluid-suspending medium boundary. The equations above assume that the packet remains spherical. Lateral forces may also be applied to the packet by dielectrophoresis. Once these exceed the effective adhesion forces joining the packet to the orifice of the tube and the column of fluid within it, the packet will sheer from the orifice and be pulled towards the collection electrode. It is to be understood that one or multiple electrodes may be configured for the purpose of injecting packets in this way and that a variety of electrode geometries may be used. Additionally, fluid packets injected previously and sitting on the electrodes may themselves distort the field in ways that can usefully be employed for modifying injection behavior.

It is to be understood that the underlying principles expressed above may be adapted to other situations and that, in general, numerical techniques known in the art such as finite element and other methods may be used to make simulations of packet injection characteristics for any desired geometry.

Figure 2:
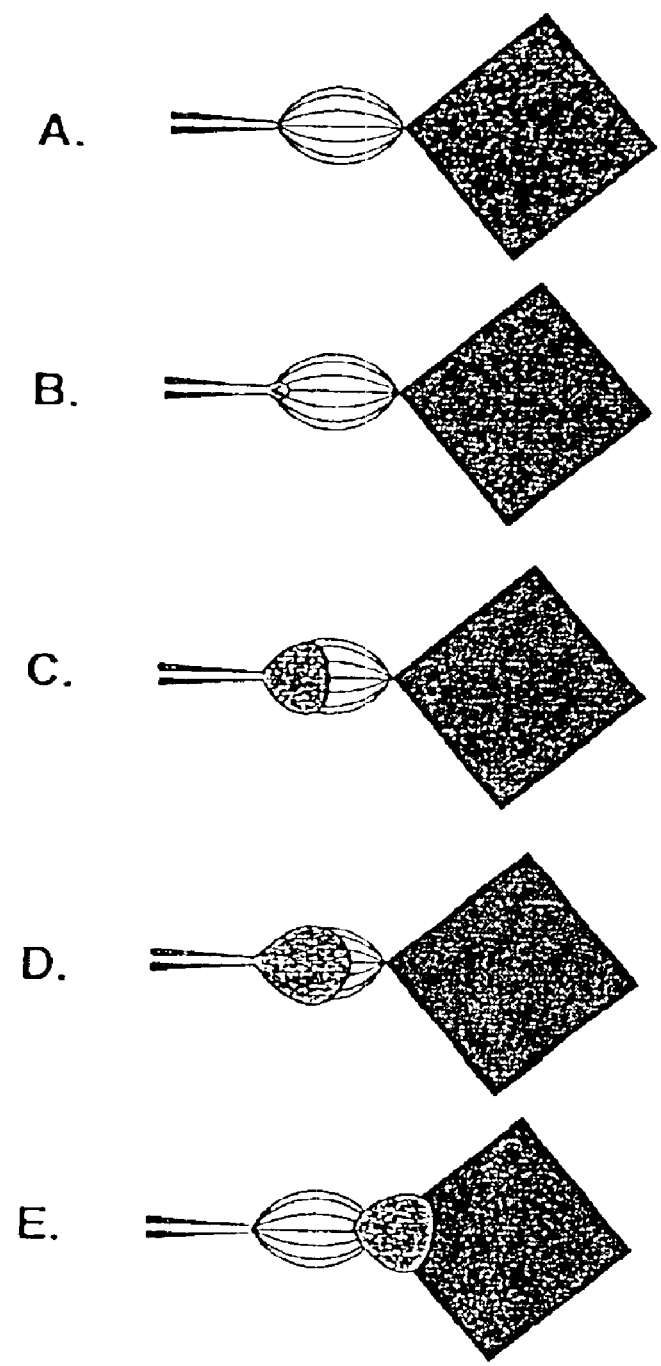
FIG. 2A, FIG. 2B, FIG. 2C FIG. 2D and FIG. 2E is a schematic that shows the stages of dielectric packet injection according to embodiments of the present disclosure.

A packet injection is shown in FIG. 2 where a hydrostatic pressure below the hold-off pressure is present in FIG. 2A, and the electrical field has just been applied to supplement the pressure and draw fluid into the packet, displacing the suspending medium. The packet grows in FIGS. 2B and 2C, but the dielectrophoretic force emanating from the field gradient close to the injection tip pulls the packet back towards the tip. Once the packet grows beyond half-way to the electrode, the dielectrophoretic force helps to increase fluid injection and pulls the packet towards the electrode. In FIG. 2E, lateral forces have overcome the cohesion between the packet, the column of fluid in the injection tube, and the tube orifice, and the packet has detached, moved to the electrode, and conformed to the high field regions surrounding the tip and edges of the electrode. In this way, and by modifying one or more of the parameters listed below in Table 1, one may consistently and automatically meter fluid packets onto any surface. In this manner, consistent, high-resolution microfluidic processing may be achieved.

The expression used above for the potential distribution V(z) is appropriate for a two-dimensional plane rather than a three dimensional space as applicable to some cases where the electrodes are planar, and the packets are manipulated on a planar surface. In other cases, three-dimensional equations may be better suited and, in still other cases, computer simulations of the type known in the art may be required when analytical solutions cannot be obtained. Nevertheless, the physical principles underlying packet formation is essentially the same in all these cases as that described here for illustrative purposes, and the magnitude of the pressure changes in the packets induced by the fields will be comparable in magnitude.

Once injection of a first packet has been accomplished, additional packets may be injected and fused with the first packet to form a larger packet. Such applications are explained in U.S. patent application Ser. No. 09/249,955, which has been incorporated by reference. In some cases, packet formation at the orifice may proceed until the forming packet becomes detached from the orifice when it touches a previously injected packet. Fluid may be metered out and packets of different sizes may be made by dielectric injection. Since the packet injection occurs under the influence of applied electrical fields in one embodiment, automated electrically controlled packet formation may readily be accomplished by switching the fields on and off, or by appropriately adjusting the signals to accomplish the injection of packets. Once injected, packets may be used in situ or else manipulated and moved to desired locations by dielectrophoresis, traveling wave dielectrophoresis, or any other suitable force mechanism following injection. Techniques for the manipulation of the packets is described in U.S. patent application Ser. No. 09/249,955.

Parameters affecting packet injection

It is instructive to examine some of the parameters that influence the pressure, size, and formation of packets injected by dielectric means. These include those listed in Table 1 below:

TABLE 1

Parameters that influence the pressure, size, and formation of packets injected by dielectric means

| | |
|---|---|
| $\gamma$ | the interfacial tension of the fluid in the suspending medium, which will be affected by surfactants and solutes in the fluid and by the properties of the suspending medium |
| $P_f$ | the hydrostatic pressure applied to the fluid in the tube and how close it is to the hold-off pressure |
| a | the diameter of the tube from which the packet formation takes place |
| $\epsilon^*_s$ | the dielectric permittivity of the suspending medium including any contribution from matter contained therein |
| $\epsilon^*_f$ | the dielectric permittivity of the fluid being injected including any contribution from matter contained therein |
| $\upsilon$ | the frequency of the applied field that effects packet formation |
| V | the applied voltage that induces packet formation (in the case of an AC field, V is the root-mean-square (RMS) voltage) |
| d | the effective distance between the tube from which the packet is injected and the electrode that creates the field. d will be an effective value if there are multiple electrodes that create the field |
| $G_{ch}$ | the geometry of the chamber into which injection occurs, including the geometry of the tube from which injection occurs |
| $G_{el}$ | the geometry of the electric field used to inject packets and manipulate them after injection resulting from the injector tube, the system of electrodes that produces the fields, and the voltages applied to or induced in each of these components. |
| $G_{fl}$ | the geometry of any packets already in the chamber and their position with respect to $G_{el}$ |

With the benefit of the present disclosure, those having skill in the art will recognize that any one, or any combination of the above factors may be modified, without undue experimentation, in order to achieve different injection characteristics.

Additional Issues

The pressure needed to remove the packet from the tube may deviate from the expressions given above if surface characteristics of the tubing make a significant contribution to the energetics of the fluid being injected. This can occur if the tubing surface has an affinity for the fluid or else has the tendency to repel it. For example, if the fluid were water, then a hydrophilic tubing surface may contribute a binding energy that may tend to hold the packet in place more strongly. In contrast, a hydrophobic surface would contribute a repulsive force that would make it easier for the packet to break free from the orifice during injection. By modifying the surface of the tube, the energetics of fluid injection may be controlled, affecting, in turn, the injection characteristics.

An example of modifying the tubing surface is the silanization of glass tubing to render it highly hydrophobic. It is much easier to separate aqueous packets from a silanized glass tube orifice than from a tube orifice that is hydrophilic.

Although the discussion above relates to dielectrophoretic force(s) aiding in the injection of a fluid packet, it will be understood that any number of different types of forces may be utilized to achieve the fluid packet injection described herein. Specifically, other separation forces may be employed. For example, acoustic and/or vibrational energy may be used to effectively shake loose a packet from an orifice. If the suspending medium is of low viscosity, such motion-induced packet separation may be inertial. On the other hand, if the suspending medium is of sufficiently high viscosity, then packet detachment may be produced by hydrodynamic drag between the packet and the suspending medium as the orifice is withdrawn sufficiently quickly. With the benefit of the present disclosure, those having skill in the art may choose to rely upon other separation forces. All such other forces sufficient to separate a fluid packet from an orifice onto a surface to achieve metered injection fall within the spirit and scope of the present application.

As used herein the specification, "a" or "an" may mean one or more. As used herein in the claim(s), when used in conjunction with the word "comprising", the words "a" or "an" may mean one or more than one. As used herein "another" may mean at least a second or more.

The following examples are included not for limitation but, rather, to demonstrate specific embodiments of the invention. It should be appreciated by those of skill in the art that the techniques disclosed in the examples which follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1
Programmable Fluid Processor

In one embodiment, packets of metered size may be injected from one or more inlet ports on the sidewall(s) of a programmable fluid processor (PFP), such as the apparatus described in U.S. patent application Ser. No. 09/249,955, by dielectrophoresis into an immiscible carrier liquid covering a reaction surface.

Fluid flow may be made to be digital, rather than continuous, in the PFP, and the packets may be controlled electronically. The only moving parts in such a setup will be the fluid packets, and no valves or mechanical pumps will be required. Injectors according to the present disclosure may be attached directly to adjacent reservoirs containing reagents or any other suitable fluid or gas. Packets may vary widely in size, but in one embodiment may have diameters from about 20 to about 100 $\mu$m. The packets may have volumes that vary widely, but in one embodiment the volumes may be in the 0.1 to 1 nL range. On-chip reservoirs according to the present disclosure having about 10 $\mu$L volumes may thus each provide up to about $10^5$ reagent packets, which would be enough for 1 assay per minute for about 60 days.

Figure 3:
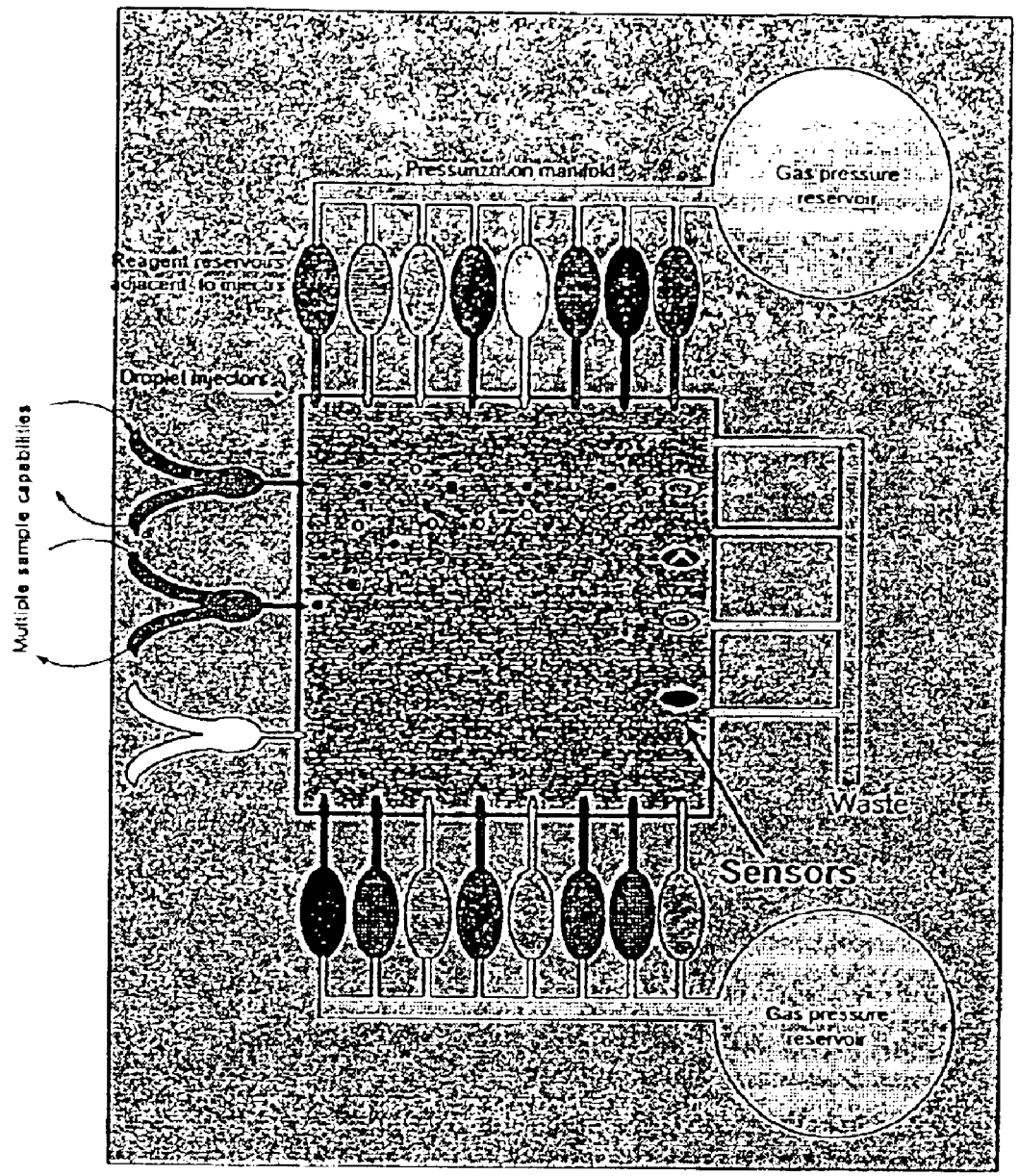
FIG. 3 is a schematic that shows a general purpose analysis apparatus according to embodiments of the present disclosure. The apparatus uses packet injection techniques as described herein.

A design of a PFP-based general-purpose bioanalysis apparatus termed a "BioFlip" is shown in FIG. 3. It is shown executing two separate assays that require the sampling of two sample streams followed by the mixing and sequencing of two reagents, taken from a choice of 16.

Samples and reagents, represented by different shadings, are present in the reservoirs and injectors in the BioFlip. Fusing of packets is illustrated, as is the ability of packet streams to cross without colliding (see disclosure contained in U.S. patent application Ser. No. 09/249,955 for details involving packet manipulation). In the processes shown, the stream of packets passes over a sensor, such as an impedance sensor, and is later routed to one of the four waste lines. The possibility of choosing from 16 reagents allows different assays to be run. Depending upon how extensive the reaction surface is made, large numbers of completely different assays may be run in parallel. The discrete nature of the packets means that the different assays may be interleaved both spatially and temporally.

As illustrated, the reservoirs may be integral with pipettes (shown as long, narrow extensions of the fluid reservoirs). Alternatively, separate fluid reservoirs may be used, and those separate reservoirs may be coupled, according to any means known in the art, to the fluid injectors, which may be micropipettes, tubes, or the like. Coupled to each of the reservoirs is a gas pressure reservoir. As described previously, gas pressure may be used to apply pressure to fluid within a reservoir so that, for example, a hold-off pressure may be achieved. The gas reservoir may be coupled to the fluid reservoir by any of the various means known in the art. As illustrated, the coupling is accomplished via a pressurization manifold. Such a manifold may include any number of valves, gauges, and other instrumentation that facilitates the monitoring and application of gas pressure to the fluid reservoirs and fluid packet injectors. Additionally, suitable optical monitoring equipment, such as CCD cameras or the like may be used to visually monitor the operation of the injectors, reservoirs, or entire system.

EXAMPLE 2
Fluid Processing System

Figure 4:
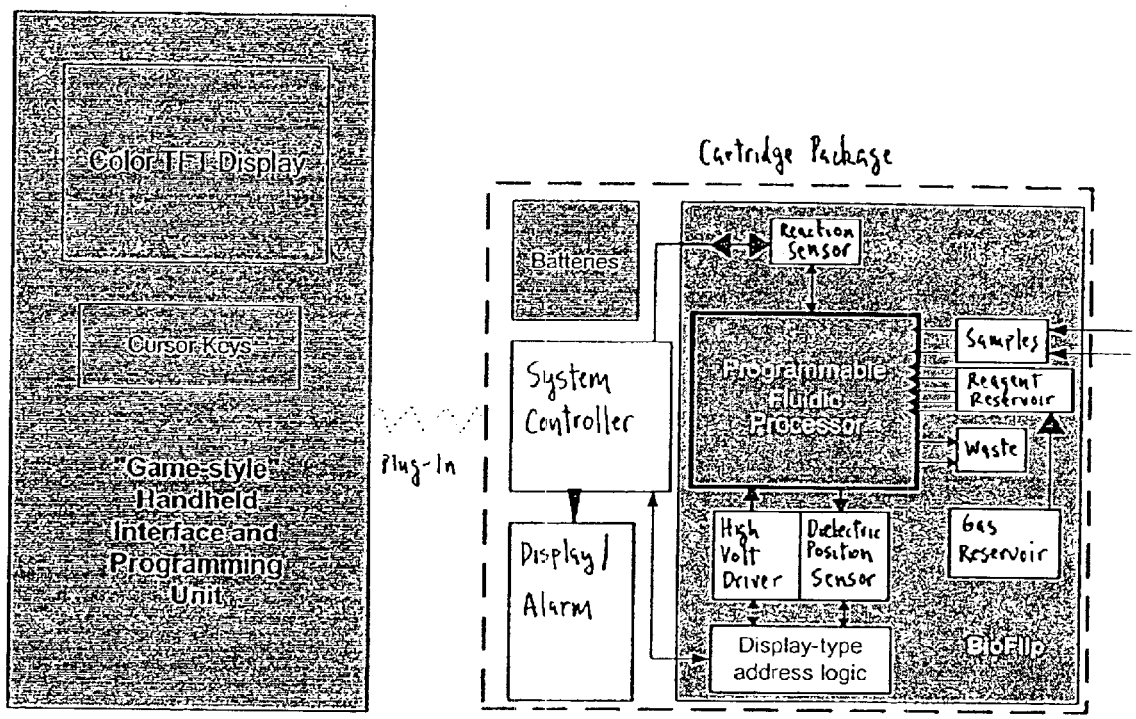
FIG. 4 is a schematic that shows another general purpose analysis apparatus according to embodiments of the present disclosure. The apparatus uses packet injection techniques as described herein.

FIG. 4 shows a block diagram of a fluid processing system that uses injection technology in accordance to the embodiments disclosed herein. On the right side of FIG. 4 is shown a fluidic processing apparatus termed the "BioFlip." This may vary in size significantly, but in one embodiment its size may be about 3"×2"×0.5". It may be in the form of a cartridge equipped with no more user interface than an alarm and a small LCD. It may be self-contained and operate autonomously. It may be programmable by a handheld unit (Windows CE or Gameboy-style) shown on its left.

The packet injection of material from the sample and reagent reservoirs may be controlled by dielectrophoresis with a no moving parts, the packet size may be controlled by varying parameters discussed above and listed in Table 1 such as orifice size and/or pressure, the packets may be moved anywhere on a two-dimensional array via dielectrophoresis or another suitable manipulation force, the packets may be fused, and chemical reactions may be made to occur when sample and reagent packets are fused on an array. Such reactions have been viewed on 2×8 and 8×8 open-top arrays of photolithographically-patterned gold electrodes on glass, driven by discrete electronics.

Figure 5:
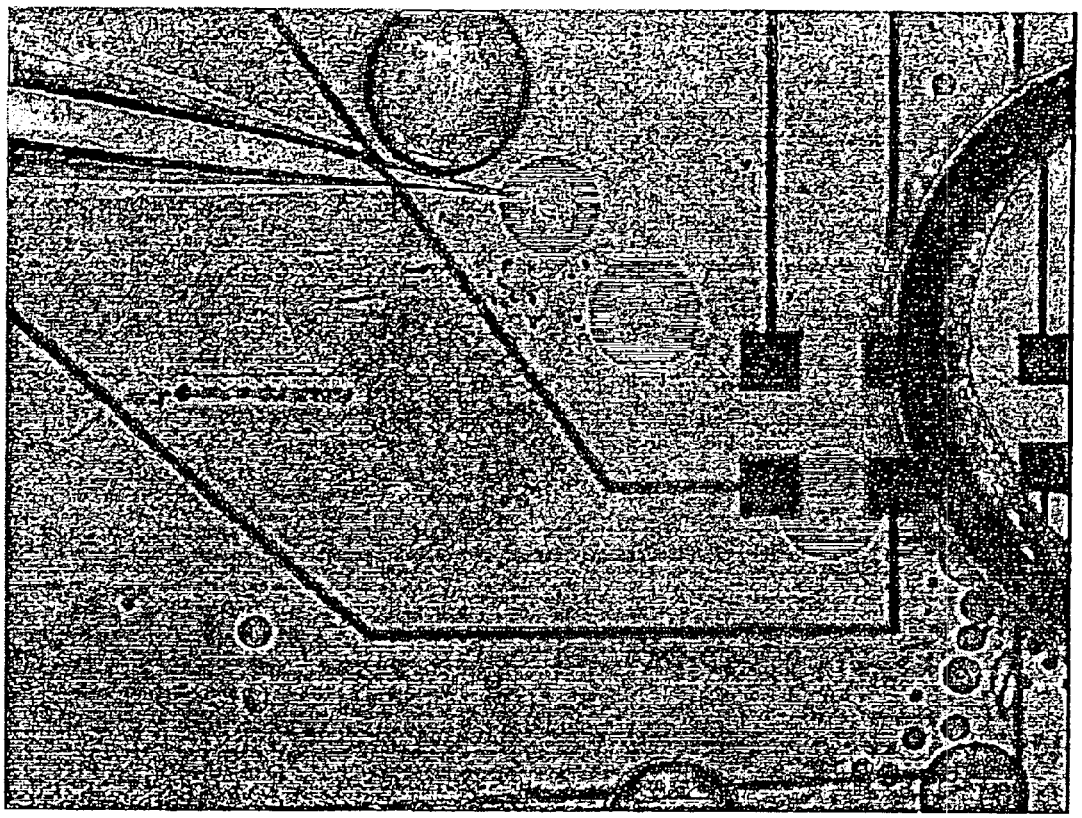
FIG. 5 is a picture that shows a stream of 57 micron packets being pulled from a micropipette tip by a dielectrophoretic field according to embodiments of the present disclosure.

A picture illustrating packet injection from a glass micropipette of about a 5 $\mu$m orifice diameter by dielectrophoresis is shown in FIG. 5. With pipette size, pipette tip to electrode spacing, pressure and AC voltage adjusted within appropriate ranges, packet size and injection rate can be electrically controlled. The picture shows, for example, a stream of 57 $\mu$m (~100 pL) packets being pulled from a micropipette tip by a dielectrophoretic field. Appropriate actuation of the field allows single or multiple packets to be injected.

Packets may be moved across the array immediately, or they may be left on a proximal electrode so that they are made to fuse with additional packets being metered onto the surface to form larger volumes with integer volume relationships. Injection rates of tens of packets per second are attainable. In the illustrated embodiment, voltages of about 100 to about 200 volts peak-peak for injection and about 30 volts peak-peak for movement were used. However, in other embodiments, these values may vary widely.

EXAMPLE 3
Pressure Relationships

The static pressure differential necessary to maintain a packet is generally expressed by:

$$P_{in} - P_{ext} = \frac{\gamma}{r}$$

where $P_{in}$ and $P_{ext}$ are the internal and external hydrostatic pressures, $\gamma$ is the surface tension and r is the radius of the packet. Thus, the pressure differential necessary to maintain a packet is inversely proportional to the radius of the packet.

Since water adheres to hydrophilic glass, injected packets tend to remain attached to the tip of the injector pipettes unless the outer surface is made hydrophobic. This may be done by dip-coating the pipettes in a anti-wetting agent such as, but not limited to, Sigmacote®, a silicone solution in heptane, or a fluoropolymer, such as PFC1601A from Cytonix, Inc.

The pressure inside a packet is inversely proportional to its radius. Therefore, if the meniscus is flat at the injector tip, it has infinite radius and zero pressure. As fluid flows to form a nascent packet, the meniscus radius decreases until the packet reaches a radius related to the injector aperture diameter, the wetting energy of the injector tip, and the interfacial energy between the packet and the immiscible suspending fluid. In this regime, pressure increases with increasing nascent packet volume, holding off fluid flow and inhibiting packet formation. Above a critical volume, however, the packet radius increases with increasing volume and the pressure in the packet decreases, encouraging fluid flow and packet formation. Thus an injector will "hold off" packet formation up to some critical hydrostatic pressure.

As long as the applied hydrostatic pressure is less than or equal to the hold off pressure, the aqueous/hydrocarbon boundary will remain stable and no fluid will be injected onto the reaction surface. However, an applied dielectrophoretic force (or other type of force) acting on the nascent packet may effectively supplement the hydrostatic force, lowering the potential barrier to packet injection. In this way, fluids may be withdrawn from the pipette onto the reaction surface using a combination of hydrostatic and dielectrophoretic forces only.

EXAMPLE 4
Injection Considerations

Figure 6:
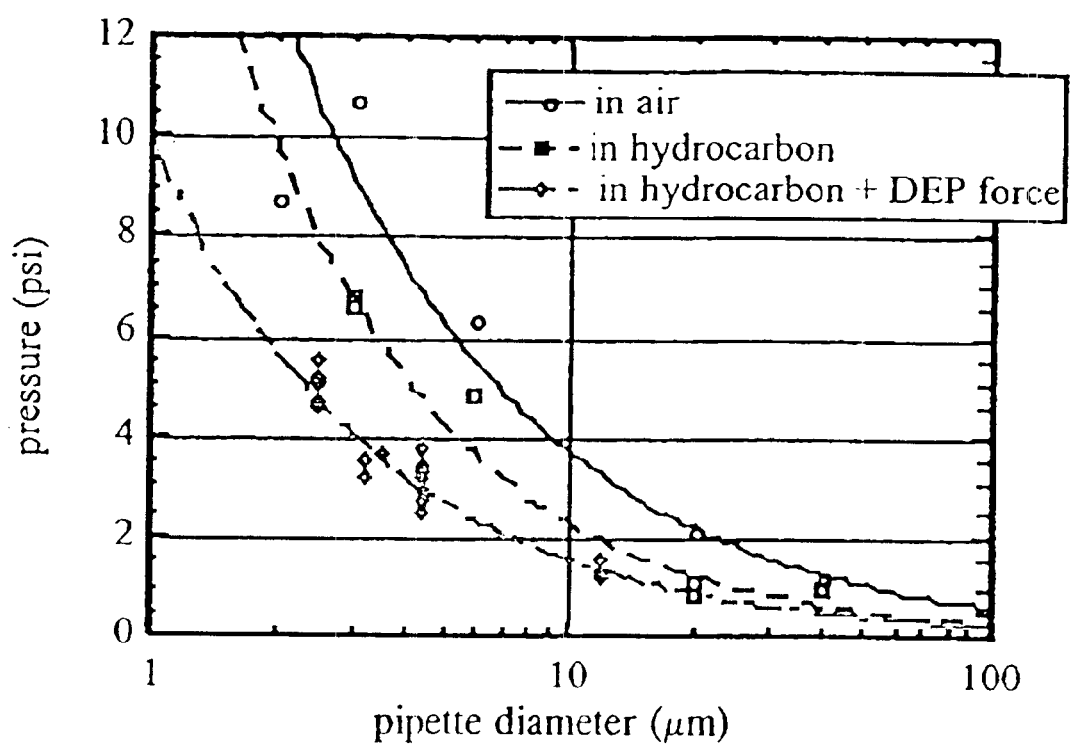
FIG. 6 is a graph that shows the relationship between pressure and pipette diameter according to embodiments of the present disclosure.

The inventors have used dielectrophoretic forces to inject aqueous packets onto 2×8 and 8×8 PFPs. The two upper curves of FIG. 6 illustrate how the static pressure necessary to spontaneously inject an aqueous packet from a pipette varies with the pipette aperture diameter and the medium into which the packet is injected. The lower curve shows how a dielectrophoretic force applied to the region around the pipette aperture reduces the static pressure at which a packet is injected. The difference between the dielectrophoretic injection pressure and the static injection pressure is the "hold off" provided by the injection aperture. By applying a sub-injection priming pressure, a true "no-moving-parts" pump using dielectrophoretic forces only, reagent packets may be injected onto a reaction surface.

FIG. 6 shows that about 8 psi is low enough to prevent spontaneous injection of an aqueous packet into a hydrocarbon from an aperture about 2.5 μm in diameter. Larger apertures hold off injection at lower pressures. Control of the diameter of injected packets may be investigated in detail as a function of pipette aperture, dielectrophoretic potential, pipette-to-electrode separation, and hold off pressure.

Packets have been injected from apertures from about 2.5 to about 12 μm in diameter, DEP potentials from about 100 to about 250 $V_{p-p}$, pipette to electrode separations from about 30 to about 300 μm, and hydrostatic pressures from about 1.3 to about 5.5 psi.

Aqueous packets have been injected onto the surface of a PFP via glass micropipettes to which water readily adheres. Dip-coating the pipettes in a anti-wetting agent such as Sigmacote®, a silicone solution in heptane, or PFC1601A from Cytonix, Inc., a fluoropolymer, reduces water adhesion and may facilitate the injection of packets onto a PFP surface.

EXAMPLE 5
Differential Meniscus Valve

In one embodiment, a differential meniscus valve may be used as a means for metering fluid packets into a programmable fluidic processor ("PFP"), and for collecting them after processing. The inventors have noted that there appears to be two distinct contributions to the behavior of trapped air bubbles, namely the relative adhesion energies of air and water to the chamber surface, and the radius of curvature of the bubble. The latter is related inversely to the bubble pressure. The differential meniscus valve of the present disclosure is designed to exploit these two properties in order to construct a valve suitable for the injection of fluid packets into a hydrophobic fluid as in PFP devices, which include programmable dielectrophoretic arrays and programmable electrophoretic arrays.

Figure 7:
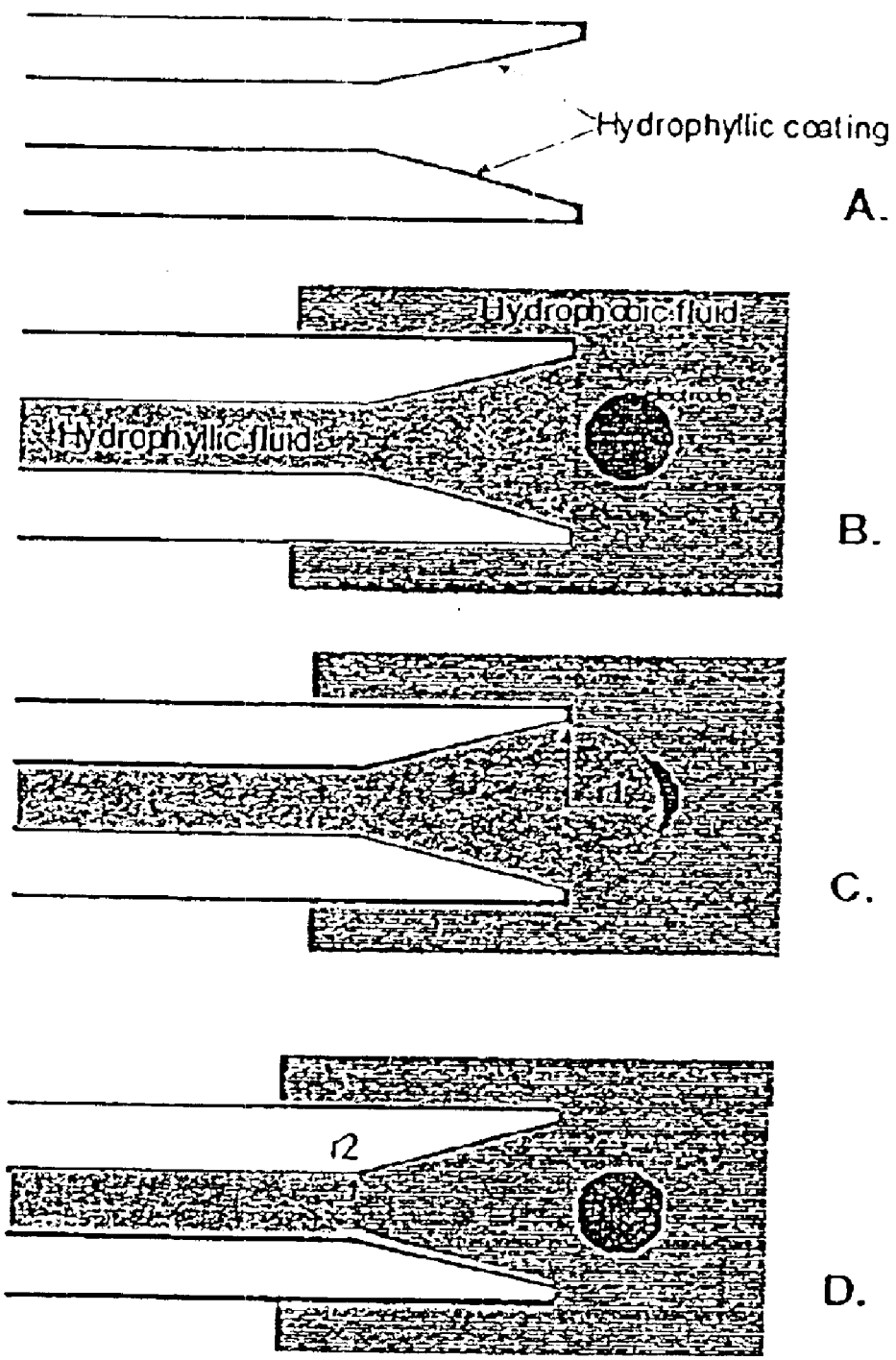
FIG. 7A, FIG. 7B, FIG. 7C and FIG. 7D show a schematic illustrating meniscus valve principles in accordance with embodiments of the present disclosure.

A differential meniscus valve is illustrated in FIG. 7. The illustrated device has no moving parts and no constrictions. The principle of operation is also illustrated in FIG. 7A. There, the PFP chamber is assumed to be to the right, the source of liquid (a reservoir or other suitable container) to be injected to the left. The microfluidic tube flares toward the end that is in the PFP chamber, and its inside is coated with a hydrophilic material. Any hydrophilic material known in the art may be used.

When the chamber and tube are filled, as in FIG. 2B, the spreading energy of the hydrophilic fluid along the hydrophilic surface tends to pull the hydrophilic fluid to the end of the flared region. If pressure is now exerted for the hydrophilic fluid end at left, as shown in FIG. 2C, a packet will begin to form. The radius of curvature as this packet forms, r1, will be controlled by the radius of the flared opening. Because this radius is large, the pressure in the packet will be relatively small. If, on the other hand, pressure is applied to drive the hydrophilic liquid into the tube, the hydrophilic surface will prevent adhesion of the hydrophobic fluid to the tube surface. The leading edge of the hydrophobic fluid will therefore be forced to assume a much smaller radius, r2, as it tries to enter the narrower section of the tube. Because r2 is smaller than r1, the pressure required to drive hydrophobic fluid into the tube will be larger than that needed to drive hydrophilic fluid in the opposite direction to form packets in the chamber.

EXAMPLE 6
Differential Meniscus Injectors

In one embodiment, a packet injector may be used that incorporates the differential meniscus valve described above. In particular, The tip of PEEK tubing connectors may incorporate the differential meniscus valve design. The tip of PEEK tubing connectors may be precision-machined to match the required injector shape, as determined by calculations using software known in the art, such as Surface Evolver software. Precision-machining provides the flexibility to create a wide range of shapes with quick turn-around time. Injectors (and collectors) may be micromachined according to techniques known in the art to increase density, and to reduce the minimum injected packet size.

An external pressure source for operating the valves may be provided by a syringe pump, pressurized reservoir, or the like. In addition, as discussed above, a dielectrophoretic force, or other suitable manipulation force may be used in conjunction with the meniscus valve injector to both inject and collect packets. The source reservoir may be coated with a hydrophobic layer that will have a small positive pressure on the watery content of the reagent, which will be attracted by the hydrophilic coating of the capillary towards the PFP chamber or surface. At the PFP interface, the packet may be pulled from the capillary into the dielectric fluid by applying a potential to one or more electrodes near the injector tip. Once inside the PFP chamber, the packet may be manipulated as desired, then positioned close to the outlet capillary.

EXAMPLE 7
Differential Meniscus Collectors

In one embodiment, packet collectors may use the meniscus valve discussed above. At an outlet capillary, another differential meniscus valve may absorb one or more packets if the field distribution among the electrode(s) close to the outlet are properly selected and switched off when the valve pulling effect is activated. One or more waste reservoirs may have an internal hydrophilic coating as well to minimize any pressure gradient that may keep the reagent inside the capillary.

EXAMPLE 8
Fabrication Examples

Low dead volume connectors may be used for interfacing microscopic fluidic components, such as syringe pumps, with microfabricated, miniature fluidic devices. A 1 mm OD connector may be made by precision machining one end of a length of PEEK tubing such that only the very tip fits within a micromachined orifice in a fluidic chip. In addition, a groove may be machined in the tubing tip to accommodate a small o-ring for creating a seal.

The inside of the tubing tip may be machined to form an appropriately-shaped nozzle. The machined PEEK tubing may then form both the fluidic connector and sample injector, a design which makes sense from an engineering standpoint since the fluidic connector is already required for introducing samples, chamber fluid, and other solutions. Furthermore, using the tubing allows for the coating of the injectors with a hydrophilic film independent of the hydrophobic chamber coating.

Injectors may be fabricated from a PEEK tubing with an outer diameter varying widely in size, but in one embodiment, its outer diameter size may be about 500 microns, and its inner diameter may be about 65 microns, which should be sufficient to produce packets between about 100 and 500 microns in diameter. In this case, a syringe pump or pressurized reservoir with an external valve may be used to inject packets into the chamber.

Injectors may be precision-machined from commercial high-performance liquid chromatography tubing. This is a very different approach to MicroFlume fabrication, which traditionally employs silicon or glass-based micromachining, or plastic molding. Unlike virtually all lithography-based micromachining techniques which are only capable of producing two-dimensional or "extruded" shapes, precision machining allows parts to be formed freely in three dimensions, with tolerances of about 5 microns (comparable to many high-aspect ratio micromachining processes). Fast turn-around on designs is another advantage of precision machining. Once optimal designs are established through precision machining, tooling can be made to mold the parts for high volume production.

Appropriate software known in the art, such as Surface Evolver, which was developed by NIST, may be used to model surface tension, pressure, and geometrical effects that determined the injected packet size. Such programs may also be used to analyze solder bump shape after reflow in the presence of electronic components and may therefore assist in design optimization.

In one embodiment, silicon micro-machining may be used to batch fabricate high-density injector arrays. Micromachining allows for smaller injectors, which will lead to smaller packet sizes, although it will be more difficult to control the injector tip geometry. Alignment of the injectors with a PFP array chip will be more precise with the micromachining approach, and this will be important to packet size, especially if dielectrophoretic forces are relied upon to pull packets into a chamber.

EXAMPLE 9
Dielectric Valve

In one embodiment of the invention, a PFP switching station is envisioned with a dielectric valve. This valve has no moving parts and can control the movement of the packet through the device based on pressure and the dielectric properties of the packet and the surrounding medium. This PFP comprises one or more injection ports, one or more exit or outlet ports and a switching station. A droplet is injected from the injection port with a pressure of:

$$P = \frac{2\gamma}{r}$$

where r is the droplet radius and γ is the interfacial tension of the droplet. The exit port, which is configured as a hydrophilic tube accepts the droplet from the surface of the device depending on the droplet pressure. The size of the exit port opening is inversely related to the pressure required for the droplet to enter the exit port. Therefore, a apparatus with a smaller exit port will require higher pressure (i.e. a smaller droplet diameter or larger droplet interfacial tension) to carry the droplet into the exit port. Varying the size of the exit ports can be used to control fluid flow through the dielectric valve.

The exit port may be any structure allowing egress from reaction surface, such as an opening in a wall or a tube. The opening may be of any suitable size or shape. Alternatively, outlet port may be a micropipette or any other equivalent device able to collect a material from reaction surface. Packets of material may be collected from reaction surface from above. A syringe or any other equivalent device may be attached to a micromanipulation stage so that packets may be precisely collected from specific locations on reaction surface. In one embodiment, the exit port may consist of a cylindrical tube opening onto reaction surface. Such a tube may have a diameter of about 1 millimeter and a length of about 3 centimeters or longer and may be coated to be hydrophilic.

The switching station can be used, for example, when it is desired to inject multiple packets from multiple vessels onto the surface. The switching station allows for the use of multiple vessels and multiple exit ports while using a single device or array, such as an array of electrodes to control the injection of packets onto the surface.

EXAMPLE 10
Holdoff Pressure

Figure 8:
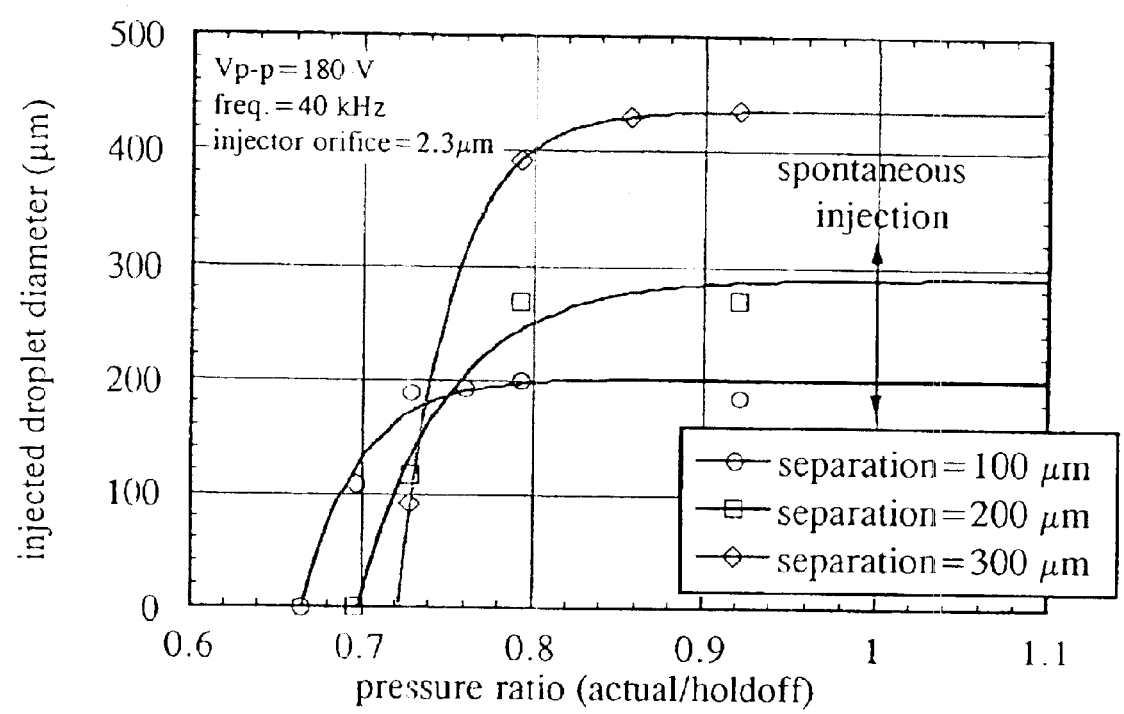
FIG. 8 is a graph that shows the relationship between the holdoff pressure ratio and the injected droplet diameter for separations of 100 μm, 200 μm and 300 μm according to embodiments of the present disclosure.

FIG. 8 illustrates the relationship between the pressure in the fluid handling system, normalized to the maximum holdoff pressure (=1), and the diameter of aqueous droplets injected onto the reaction surface. An injector orifice was positioned near a 100 micrometer ($\mu$m) square electrode that was energized with an AC electric potential (the dielectrophoretic, or DEP, field). The applied DEP field was 180 volts peak-to-peak (Vp-p) at 40 kHz. The injector orifice was 2.3 $\mu$m in diameter, separated from the edge of the active electrode by 100, 200, or 300 $\mu$m. FIG. 8 illustrates that under these conditions DEP droplet injection will not occur when the fluid handling system is pressurized below 0.65 times the maximum holdoff pressure. Also, as the system is pressurized to 0.75 to 0.85 times the maximum holdoff pressure droplets of a fixed size, corresponding to the separation distance plus the electrode width of 100 $\mu$m will be injected onto the reaction surface. In the pressure region between 0.65 and 0.85 times the maximum holdoff pressure droplets, or fluid aliquots, of intermediate, controllable, and repeatable diameter are produced. The lines on the graph in FIG. 8 are curves of the form $a*exp^{-(b-c)/d}$ fitted to the data for each separation distance.

Figure 9:
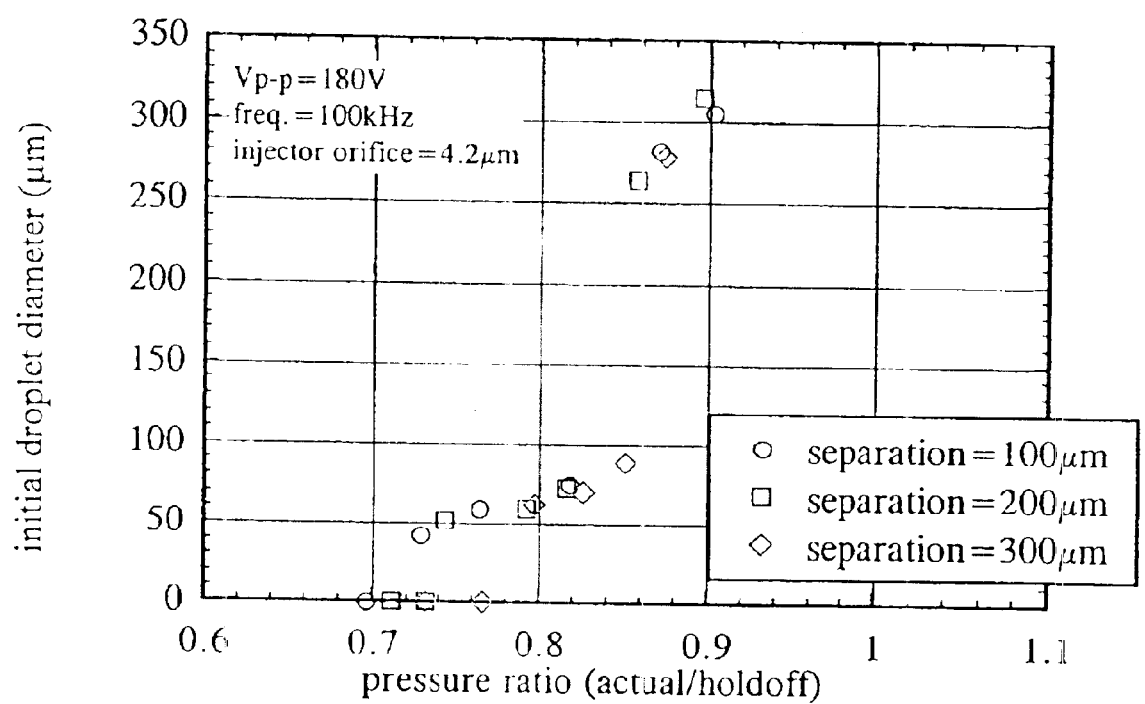
FIG. 9 is a graph that shows the relationship between the holdoff pressure ratio and the initial droplet diameter for separations of 100 μm, 200 μm and 300 μm according to embodiments of the present disclosure.

FIG. 9 illustrates the relationship between the pressure in the fluid handling system, normalized to the maximum holdoff pressure (=1), and the diameter of aqueous droplets injected onto the reaction surface. An injector orifice was positioned near a 100 micrometer ($\mu$m) square electrode that was energized with an AC electric potential (the dielectrophoretic, or DEP, field). The applied DEP field was 180 volts peak-to-peak (Vp-p) at 100 kHz. The injector orifice was 4.2 $\mu$m in diameter, separated from the edge of the active electrode by 100, 200, or 300 $\mu$m. FIG. 9 illustrates that under these conditions DEP droplet injection will not occur when the fluid handling system is pressurized below 0.7 times the maximum holdoff pressure. Also, as the system is pressurized above 0.86 times the maximum holdoff pressure droplets of a fixed size, approximately 300 $\mu$m (14 nanoliters) will be injected onto the reaction surface. In the pressure region between 0.7 and 0.85 times the maximum holdoff pressure droplets, or fluid aliquots, of intermediate, controllable, and repeatable diameter are produced.

EXAMPLE 11
Flow-Through Injector

A vessel containing a flow-through injector may be used in an embodiment of this invention. The vessels allows for sample to flow past the injector tip, preferably at a slow flow rate. This allows for the purging of the a few drops of sample such that there will always be fresh sample at the injector tip.

EXAMPLE 12
Dielectric Gate

In this example, embodiments are discussed that relate to the application of a dielectrophoretic injector that may be used for controlling the flow of fluid from a pressurized reservoir to a fluidic or microfluidic device, which may be kept at a lower pressure.

In one embodiment, a fluid reservoir supplies fluid to an inlet of a region containing one or more electrodes via a fluid pathway. The fluid pathway may include a tube, channel, or pathway defined by hydrophilic or hydrophobic surface coatings configured to provide a preferential direction of flow for the fluid from the reservoir to the region. One or more similar or dissimilar fluid outlet pathways configured to provide connections to one or more fluidic or microfluidic devices may also connected to the region.

The region may be contained within walls that form a chamber or may include an area of a surface or volume inside a larger volume. The region may be configured to provide a hydrophilic or hydrophobic barrier to the flow of fluid from the reservoir to one or more of the fluid outlet pathways leading to the fluidic or microfluidic devices.

The pressure in the reservoir and the properties of the region may be configured so that fluid flow across the region does not occur spontaneously. Instead, the fluid flow may be precisely controlled by way of one or more electrodes or other mechanisms configured to apply an electric field. In one embodiment, electrodes in the region may be connected to a control circuit capable of providing AC or DC electrical signals. The inventors have coined a region configured in this manner—a region including electrodes for precisely controlling flow via dielectric forces—as constituting a "dielectric gate." When an electrode in proximity to the fluid inlet is energized by an appropriate electrical signal, dielectric forces draw fluid from the inlet pathway. Switching of the electrical signal to the electrodes and, optionally, additional electrodes within the region result in the transfer on one or more droplets of fluid from the inlet pathway to one or more outlet pathways. Changing the signal excitation results in cessation of fluid flow.

Therefore, by applying an appropriate sequence of electrical signals to one or more electrodes in the region, fluid flow from the reservoir to one or more conventional fluidic or microfluidic devices may be precisely, electronically controlled. Droplets may be of well-defined volume, and the control circuit may be configured to count the number of droplets transferred from the inlet to the outlet pathways. Such counting may be accomplished, in one embodiment, using one or more impedance sensors. Therefore, the dielectric gate disclosed in this example may be used as a method to control fluid flow rate and to accurately meter the volume of fluid transferred if desired. As will be understood by those having skill in the art, the reservoir, dielectric gate, and fluidic device(s) may be discrete or integrated within a single chip.

Figure 10:
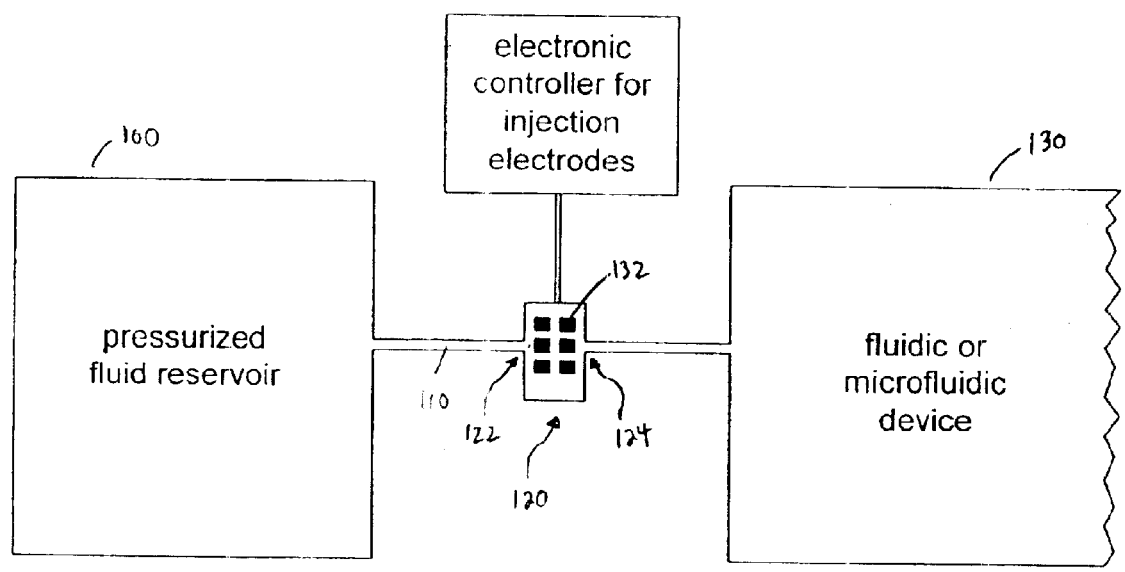
FIG. 10 is a schematic diagram of a dielectric gate according to embodiments of the present disclosure.
Figure 11:
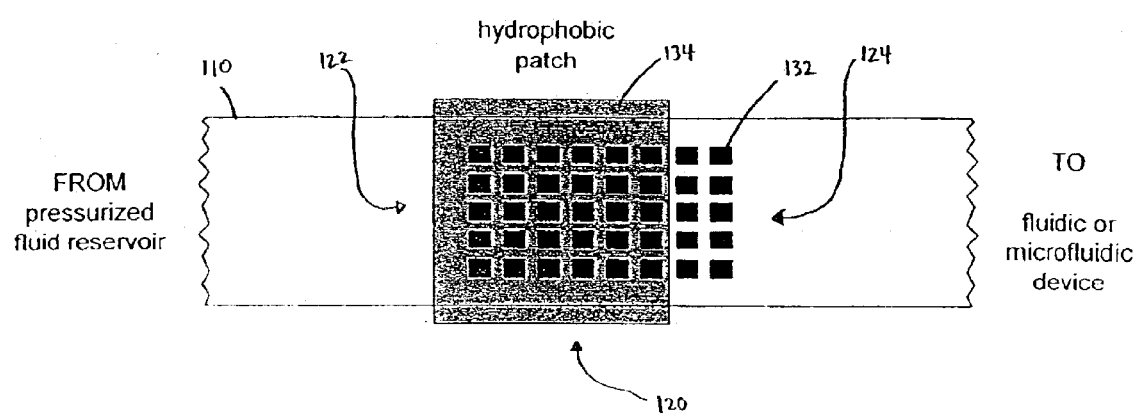
FIG. 11 is another schematic diagram of a dielectric gate according to embodiments of the present disclosure.

FIGS. 10 and 11 illustrate specific embodiments concerning dielectric gates. In the embodiment of FIG. 10, the fluid reservoir 100 includes a container that is pressurized and connected via channel 110 to dielectric gate 120. The inlet portion 122 of dielectric gate 120 may include an injector of any type described herein.

An outlet portion 124 is provided to lead fluid from dielectric gate 120 to a fluidic or microfluidic device 130, which in different embodiments may include, for example, a capillary electrophoresis, polymerase chain reaction, DEP-FFF, bioflip, or any other fluidic system.

Electrodes 132 may be operated as described herein and in U.S. Pat. No. 6,294,063, which has been incorporated by reference, so as to draw droplets from the inlet injector adjacent inlet portion 122 and transfer them to outlet portion 124. In different embodiments, dielectric gate 120 may be filled with air, gas, or a dielectric partitioning medium.

In one embodiment, the injector and/or outlets of dielectric gate 120 may be treated with hydrophilic or hydrophobic coatings to enhance the separation of droplets from the injector and the collection of droplets at the output portion 124.

FIG. 11 illustrates an embodiment in which the reservoir and inlet and outlet pathways may include hydrophilic tracks on a surface that is otherwise hydrophobic. The surface may be within a channel or tube or may be patterned on a larger surface so that the fluid is contained within "virtual channels" defined by the hydrophilic pattern.

The pathway from the reservoir may be broken by a hydrophobic patch 134 in the vicinity of one or more electrodes 132. The application of one or more electrical signals to the electrodes in an appropriate sequence induces fluid flow across hydrophobic patch 134 and through the exit pathways 124 leading to microfluidic or fluidic stages.

Removal of the electrical signals results in cessation of fluid flow across the patch 134. In this way, fluid flow can be precisely, electronically controlled or metered with no moving mechanical parts.

In different embodiments, dielectric gate 120 may be configured to have one or more outlet pathways, allowing multiple fluidic systems to be controlled by a single dielectric gate.

As will be appreciated by those having skill in the art, the teachings of this disclosure, and particularly this example, provide a no-moving parts mechanism for precision valving, dispensing, and metering fluids into microfluidic systems for chemical and biological applications, eliminating the need for pumps and mechanical valves. Applications for such technology are vast and include but are not limited to: controlling and metering fluid flow in microanalysis, lab-on-a-chip, micro synthesizers, capillary electrophoresis, gene chips, and other fluidic devices.

EXAMPLE 13
Theoretical and Experimental Considerations I

The size of injected droplets taught herein may be understood in much the same way as one can calculate the size of droplets dripping from a tap. At flow rates typically involved, and especially when the injection of a viscous fluid into another viscous suspending medium is considered, one may to a reasonable approximation neglect inertial effects and assume that low Reynolds number flow characteristics prevail. Once a DEP force field has been established to overcome the hold off conditions for droplet formation, the droplet will continue to inflate at the orifice until the lateral DEP forces pulling the droplet away from the orifice exceed the surface tension forces that hold the droplet at the orifice. The forces will balance when the droplet attains a volume $$\Lambda = \frac{2}{3}\pi\left(\frac{a\gamma}{\varepsilon_m f_{CM} \overline{E} \cdot \frac{\partial \overline{E}}{\partial x}}\right) \qquad 13\text{-}1$$

Here a is the orifice diameter, γ is the droplet/medium interfacial tension, and $\partial \overline{E}/\partial x$ is the electric field gradient that leads the droplet to be pulled away from the orifice. As soon as that volume is exceeded by an infinitesimal amount the droplet will be pulled from the orifice by the DEP force and will therefore have been injected. Since the field and field gradient both vary with the applied voltage, V, and are determined by the geometry of the injector-electrode configuration, the injected droplet volume can, for a given geometry G, be approximated.

$$\Lambda = \frac{2}{3}\pi\left(\frac{a\gamma}{\varepsilon_m f_{CM} G V^2}\right) \qquad 13\text{-}2$$

Note that the injected droplet size will increase with orifice diameter, a, but decrease with the square of the injection voltage. This offers opportunities to control the droplet size by modifying V. Thus droplets will form as long as V is sufficiently large to overcome the hold off pressure as discussed earlier and the size of the injected droplets can be increased by keeping V as low as possible to meet that criterion or decreased by making V large. The geometry term G is dominated by the electrode and chamber geometries but may also include contributions from other droplets already injected into the chamber. The droplet interfacial tension, γ, may be modified as γ' to take into account any energy effects associated with the contact between the droplet and the circumference of the injector tip. This, then, confirms that hydrophilic and hydrophobic tips have different injection properties.

If the injection voltage is maintained after a droplet is injected then another droplet will immediately begin to form. However, the hydrodynamic resistance of the injector tube and orifice limit the rate of fluid flow and, therefore, the rate of droplet formation. The hydrodynamic resistance depends on the length and bore of the pathway that supplies liquid to the orifice. Again assuming low Reynolds number flow, and assuming that the pathway is of circular cross section and diameter a, length L, the fluid viscosity is η, and the flow rate Φ corresponding to a pressure P is given by the Poiseuille equation $$\Phi = \frac{\pi a^4}{128 \eta L} P \qquad 13\text{-}3$$

To accurately calculate the time taken to fill each droplet to the volume at which DEP forces will pull it from the orifice requires the precise variation of droplet pressure with droplet volume to be taken into account. But to illustrate the physics, the approximate expression for the contribution to droplet pressure induced by the DEP field is:

$$P_{DEP} \approx \frac{\varepsilon_m}{4} f_{CM}\left(\frac{V}{2r}\right)^2 \qquad 13\text{-}4$$

The net pressure driving droplet formation will be the sum of all pressure components, namely the sum of the hydrostatic pressure applied to the system, $P_{hydro}$, the DEP induced pressure, $P_{DEP}$, and the back pressure from the droplet surface, $P_{meniscus}$, $$P_{net} = P_{hydro} + P_{DEP} + P_{meniscus} \qquad 13\text{-}5$$

The flow of fluid into the droplet may therefore be written $$\Phi = \frac{\pi a^4}{128 \eta L}(P_{hydro} + P_{DEP} - P_{meniscus}) \qquad 13\text{-}6$$

Substituting for the expressions for $P_{DEP}$ and $P_{meniscus}$, one obtains $$\Phi = \frac{\pi a^4}{128 \eta L}\left(P_{hydro} + \frac{\varepsilon_s f_{CM} V_{DEP}^2}{16 r^2} - \frac{2\gamma}{r}\right) \qquad 13\text{-}7$$

Assuming that $P_{hydro}$ is below the holdoff pressure, Eqn. 13–7 shows that the application of a sufficiently high DEP voltage can initiate flow to form a droplet with diameter larger than 2a that will continue to fill if $V_{DEP}$ is removed, i.e., $$P_{hydro} - \frac{2\gamma}{r} > 0 \qquad 13\text{-}8$$

One also notes that as the droplets attain a radius r>>a, then the terms with r in the denominator become small and the flow is driven predominantly by $P_{hydro}$. When a droplet finally attains sufficient size to be torn away from the injector tip by the lateral DEP force component, additional droplets will form if the DEP field is still applied. This is predicted to occur at a volume $$\Lambda = \frac{2}{3}\pi\left(\frac{a\gamma'}{\varepsilon_s f_{CM} G V_{DEP}^2}\right) \qquad 13\text{-}9$$

The diameter of the droplet will then be given by $$D = \frac{3}{4\pi}\left[\frac{2}{3}\pi\left(\frac{a\gamma'}{\varepsilon_s f_{CM} G V_{DEP}^2}\right)\right]^{1/3} \qquad 13\text{-}10$$

Or $$D = \left[\frac{9a\gamma'}{32\pi^2 \varepsilon_s f_{CM} G V_{DEP}^2}\right]^{1/3} \qquad 13\text{-}11$$

That is $$D \propto V_{DEP}^{-2/3} \qquad 13\text{-}12$$

$$D \propto a^{1/3}$$

This shows that when $V_{DEP}$ is low the droplet will grow to large size, e.g., reaching the electrode, but that when $V_{DEP}$ is high, smaller droplets may be produced. Eqn. 13–12 also predicts a fairly weak dependency of injected droplet diameter on orifice size.

The volume of the injected droplets, $\Lambda$, is given in Eqn. 13–9. Assuming that the injected droplets have a diameter D>>2a, then, to a first approximation, the rate of droplet injection, R, will be proportional to $\Phi$, which, in turn depends predominantly on $P_{hydro}$ during most of the injection process.

EXAMPLE 14
Theoretical and Experimental Considerations II

Principal factors governing DEP injection include injector orifice diameter, fluid system pressure, P, DEP potential, $V_{DEP}$, and injector orifice-electrode spacing, Z. In this example, these factors are explored to determine their effect on the injection process.

Experimental Design

In one embodiment, the inventors uses ~113 µl of 1-bromododecane to serve as a dielectric medium. Micropipette injectors, filled with de-gassed, triply-distilled water ($3XH_2O$), were maneuvered adjacent to an electrode on an open edge, i.e., a side of the array where the electrodes were not obscured by leads, of the array using a Huxley-Wahl micromanipulator. Injector height above the reaction surface was controlled by elevating a microscope stage into focus, lowering the stage a predetermined number of "ticks" on the vertical axis control knob, then using the vertical axis of the micromanipulator to bring the injector orifice into focus. This process had to be iterative since the pipette was being maneuvered in the liquid dielectric medium (index of refraction=1.46) which modified the focal plane. In general, the injector was kept 10–20 µm above the reaction surface. Contact between the glass injector tip and the reaction surface was typically catastrophic for the injector in this embodiment.

DEP injection was tested by placing the injector orifice adjacent to an electrode on the edge of an 8×8 electrode array. The amplitude and frequency of the DEP voltage, $V_{DEP}$ and $f_{DEP}$ respectively, were controlled from an external DC power supply and function generator. The lateral distance from the injector orifice to the edge of the electrode, Z, was controlled by the Huxley-Wahl micromanipulator. A manually operated syringe pump was used to control the pressure, P, of the droplet fluid in the fluid handling system, and a custom-built pressure sensor circuit monitored the pressure. Each experimental sequence of droplet injection was videotaped, and each set of parameters was referenced against a frame counter that recorded the experiment sequence number.

Measurements of Hydrostatic Holdoff

The pressure differential across a droplet boundary was directly related to the interfacial tension and inversely related to the droplet radius. In the case of droplet injection, the nascent droplet radius was a function of the orifice diameter from which the droplet fluid was extruded. To establish appropriate pressure limits for each injection experiment, a measurement was made of the pressure at which a droplet was first expelled from the injector orifice with no applied DEP field, i.e., the holdoff pressure. This measurement involved raising the pressure within the fluid handling system very gradually, as sudden changes in pressure within the rigid-walled, small-volume, fluid handling system would propagate a pressure wave to the orifice, expelling fluid at mean pressures that were below the true holdoff pressure.

Figure 12:
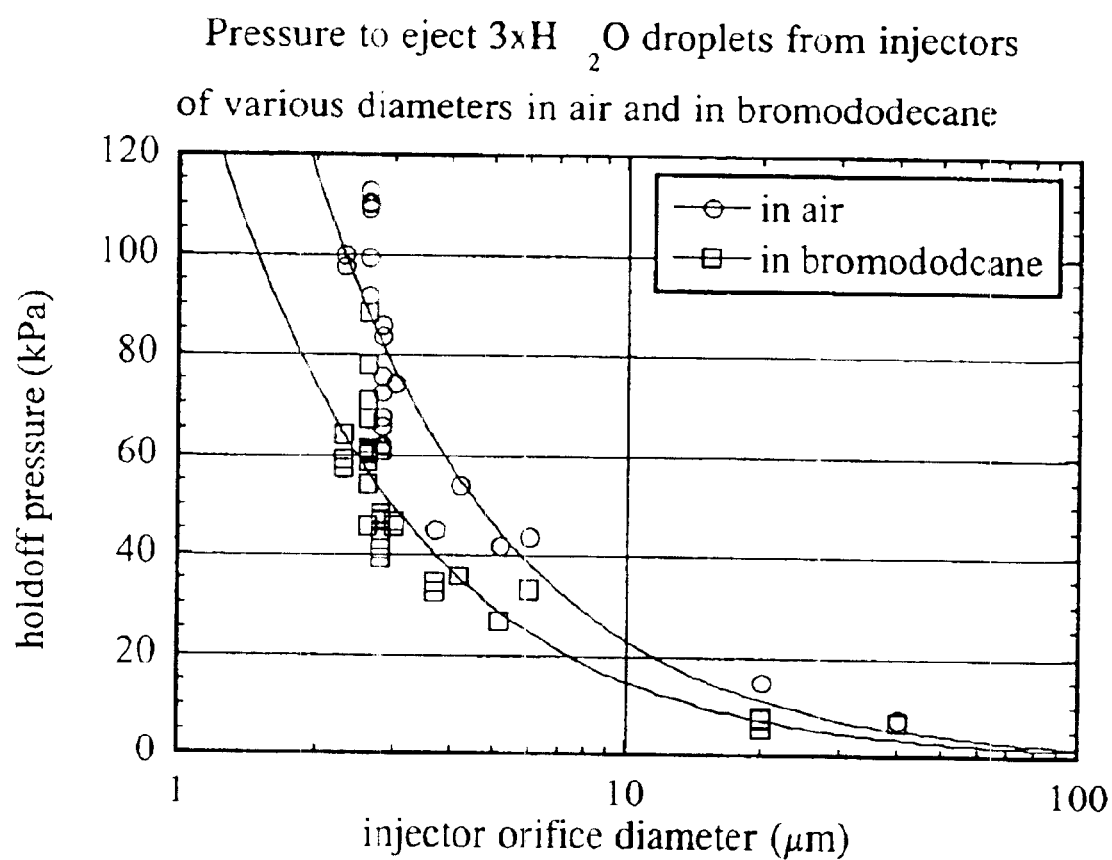
FIG. 12 is a graph illustrating aspects of the present disclosure. It shows that holdoff pressure is a function of the injector orifice. The measured holdoff pressure in kPa is plotted against injector orifice diameter in μm with the injector orifice in open air (circles), and immersed in 1-bromododecane (squares). Measurements were made using injector orifices from 2.6 to 40 μm in diameter. The two curves reflect the differences in interfacial tension of the water/air system (72.0 dyne/cm), and the water/bromododecane system (52.6 dyne/cm).

Measurement of holdoff pressure was made with the injector orifice in open air, and again when it was immersed in the 1-bromododecane dielectric medium. Results for a number of different experiments using injector orifices from 2.6 to 40 µm in diameter are graphed in FIG. 12. The different curves for the air and 1-bromododecane conditions reflect the differences in interfacial tension of the water/air system, and the water/bromododecane system. Data are shown fitted with curves of the form:

$$P = \frac{\text{constant}}{\text{injector radius}} \qquad 14\text{-}1$$

Injection Threshold Versus $V_{DEP}$

Measurements were made to determine how changes in the applied DEP field would affect the pressure at which droplets would be injected. As before, the injector was positioned above the reaction surface using a Huxley-Wahl micromanipulator. The DEP voltage was set to 120, 180, or 250 $V_{p\text{-}p}$, the videotape system was activated, and the fluid handling system was slowly pressurized using the manual syringe.

Figure 13:
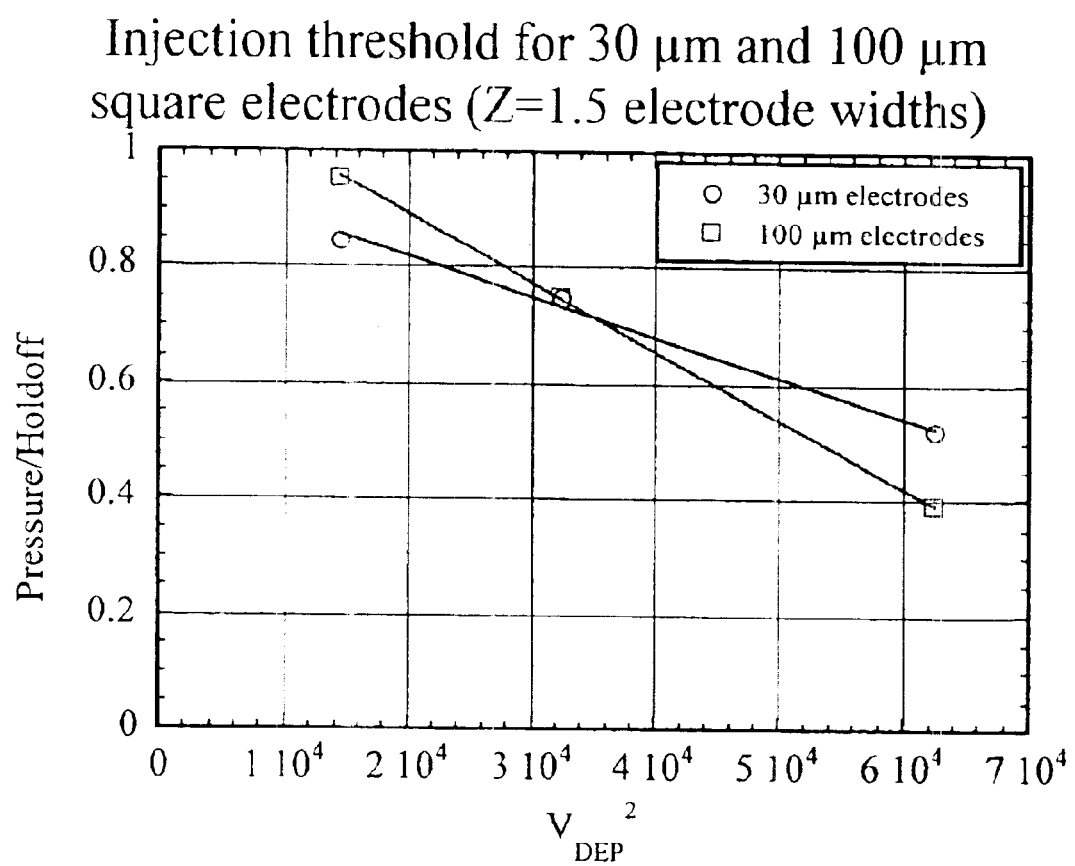
FIG. 13 is a graph illustrating aspects of the present disclosure. It shows threshold pressure vs. $V_{DEP}^2$ for droplet injection. The threshold pressure at which a droplet was injected is seen to be a linear function of $V_{DEP}^2$. Increasing $V_{DEP}$ lowers the threshold pressure at which the applied DEP field can inject droplets. The holdoff pressure measured for the injector with no applied field (P/H=1) normalizes the threshold pressure at which droplet injection occurs. In both cases illustrated the injector orifice diameter was 2.6 μm and its interior had been treated with FluoroPel® to render it hydrophobic. The distance, Z, between the injector orifice and the edge of the active electrode was 1.5 times the electrode width, i.e., 45 μm for the 30 μm electrode and 150 μm for the 100 μm electrode. The plotted $V_{DEP}^2$ corresponds to applied DEP potentials of 120, 180, and 250 Vp-p. This relationship strongly suggests that a dielectric energy effect is responsible for the injection.

FIG. 13 illustrates how increasing $V_{DEP}$ lowers the injection pressure in the case of two different electrode array sizes. In FIG. 13 the holdoff pressure measured for the injector with no applied field (P/H=1) normalizes the threshold pressure at which droplet injection occurs. In both cases illustrated, the injector orifice was 2.6 µm in diameter. The interior of the orifice had been treated with FluoroPel® to render it hydrophobic. The distance, Z, between the injector orifice and the edge of the active electrode was, in both cases 1.5 times the electrode width, i.e., 45 µm for the 30-µm electrode and 150 µm for the 100-µm electrode. The relationship between $V_{DEP}^2$ and the P/H at which injection commences was found to be linear.

Pressure Versus Injected Droplet Diameter and Injection Rate

In order to determine the relationship between the fluid handling system pressure and the size of injected droplets and their injection rate, experiments were conducted under conditions of fixed injector orifice diameter (2.6 µm), electrode size (30 µm squares), and injector-electrode separation (100 µm).

As before, the injector was positioned above the reaction surface using a Huxley-Wahl micromanipulator. The DEP voltage was set to 120 $V_{p-p}$, and the fluid handling system pressurized using the manual syringe to various levels between 60% and 90% of the measured holdoff pressure in bromododecane. The videotape system was activated, and the DEP voltage, $V_{DEP}$=120, was switched on.

Figure 14:
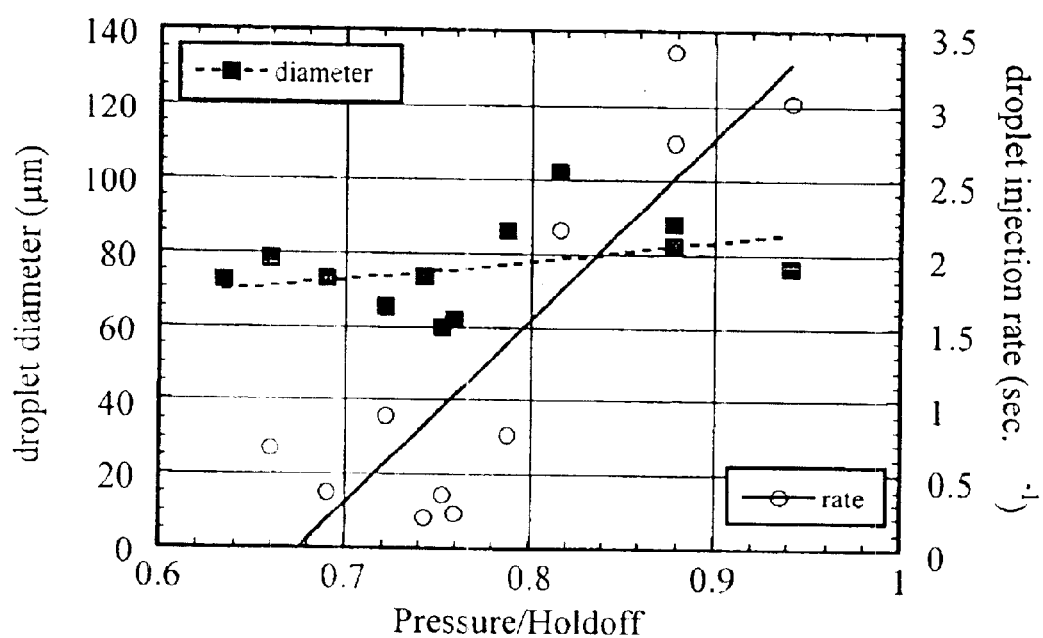
FIG. 14 is a graph illustrating aspects of the present disclosure. It shows injected droplet diameter and rate vs. pressure. Injected droplet diameters are essentially independent of the applied-pressure/holdoff-pressure ratio (P/H) of the fluid handling system, but the droplet injection rate increases rapidly as system pressure approaches the holdoff value. A 2.6 μm-diameter injector was placed 100 μm from an active electrode measuring 30 μm on a side. The fluid system pressure was set at various points between 60 and 90% of the holdoff pressure when the DEP field ($V_{DEP}$=120) was activated. As the fluid system pressure approached the holdoff pressure (P/H=1) the droplet injection rate increased rapidly while the radii of injected droplets remained essentially unchanged. The droplet injection rates and radii are fitted with linear curves.

The rate of droplet injection was determined by counting the number of video frames (@ 30 frames per second) between injection of the first and second droplets. FIG. 14 shows that as the fluid system pressure approached the holdoff pressure (P/H=1) the droplet injection rate increased rapidly while the radii of injected droplets remained essentially unchanged.

It will be recalled that Eqn. 13–6 implies that the droplet flow rate is a linear function of the hydrodynamic pressure, $P_{hydro}$. For this reason the droplet injection rate and radii may be fitted with linear curves of the form $$\Phi(\text{or } r) = \frac{\text{constant}}{(P/H)} \quad 14\text{-}2$$

Distance and Voltage Dependence

Experiments were conducted to determine the effect of varying the injector-electrode separation on the diameter of injected droplets. The injector was positioned above the reaction surface using a Huxley-Wahl micromanipulator, the DEP voltage was set, the fluid handling system was pressurized using the manual syringe, and the videotape system was activated.

Figure 15:
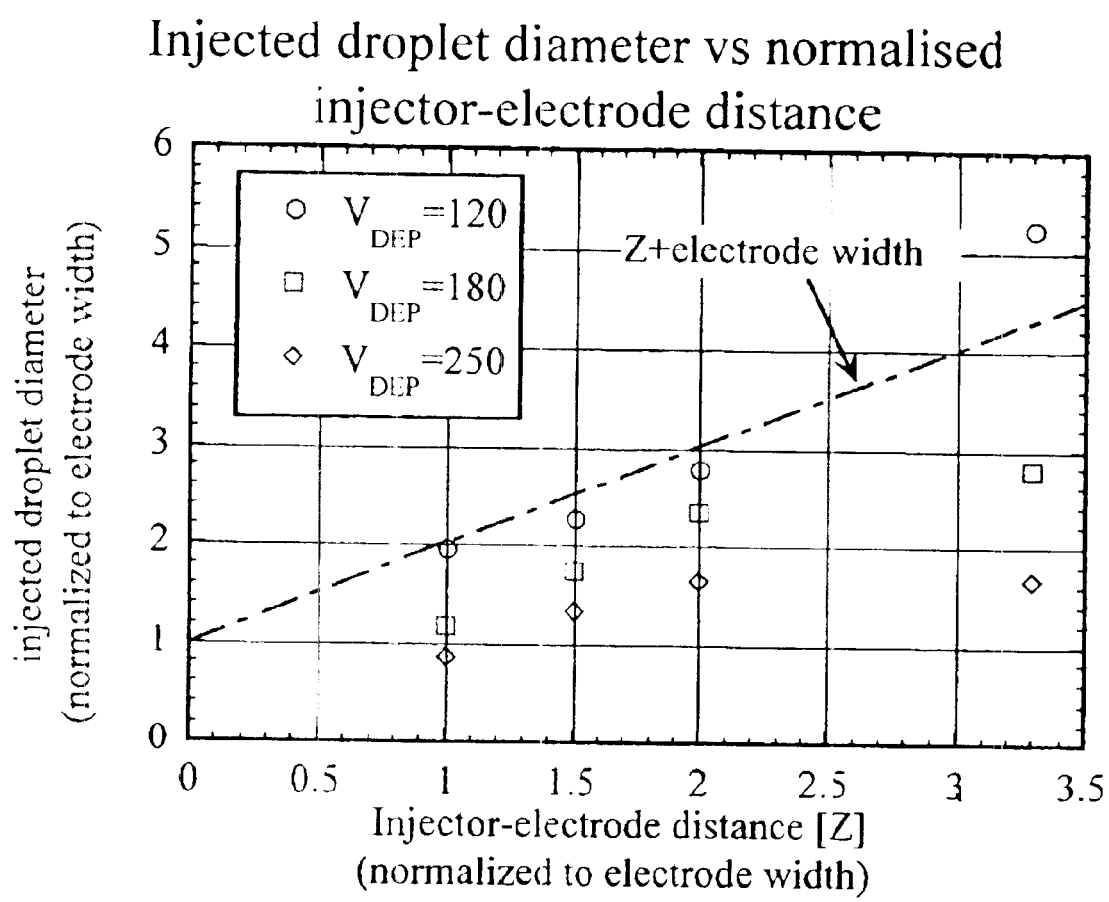
FIG. 15 is a graph illustrating aspects of the present disclosure. It shows injected droplet diameter as a function of $V_{DEP}$. Injected droplet diameters were found to vary with $V_{DEP}$ for fixed injection geometries. Here, a silanized injector 2.6 μm in diameter was placed at various distances, Z, from the edge of an active electrode. At $V_{DEP}$=120 droplets were drawn from the injector until they covered the active electrode and the electrode-injector gap, Z. With progressively higher DEP fields, injected droplets became smaller and their diameters became independent of Z.

FIG. 15 graphs the results of a set of injections carried out under conditions of fixed injector orifice diameter (2.6 µm) and electrode array size (square electrodes, 30 µm on a side, with 30 µm spacings). Three different voltages, 120, 180, and 250 $V_{p-p}$ @ 60 kHz were applied with the injector orifice positioned 30, 45, 60, and 100 µm from the energized electrode. The fluid system pressure was set at P/H=0.90 @ 120V, 0.81 @ 180V, and 0.71 @ 250 V. The orifice interior was silanized with FluoroPel® to render it hydrophobic.

Under different applied field conditions, an applied DEP field may stimulate two distinct modes of fluid injection. In one mode, which was characteristic of low DEP fields, fluid was drawn from the orifice to form a steadily expanding drop of fluid in the chamber that did not detach from the injector. In the other mode, which was characteristic of higher DEP fields, expanding droplets of fluid broke free from the orifice when they reached a well-defined size, and moved rapidly to the energized electrode some distance away under the influence of lateral DEP forces.

Droplet diameters, shown on the vertical axis of FIG. 15, are normalized to the length of the electrode edge to illustrate the tendency for low applied DEP fields to draw liquid into the chamber without it detaching from the orifice, rather than to inject discrete droplets from the injector. The dashed line in FIG. 15 marks the Z+electrode width contour corresponding to the condition that droplets grew large enough to completely fill the gap between injector and electrode. At $V_{DEP}$=120 (circles) fluid was drawn from the injector orifice continuously until a droplet formed that approximately spanned the width active electrode (30 µm) and the space between the electrode and the injector (Z). As the injector-electrode spacing was increased, droplets drawn at $V_{DEP}$=120 grew even larger, tending toward the spontaneous injection case. At higher $V_{DEP}$ drops also grew with increasing Z, but were injected from the orifice as discrete droplets as evidenced by their diameters trending well below the dashed line. With increasing separation, droplet diameters at $V_{DEP}$=180 and 250 leveled off and became independent of Z.

Figure 16:
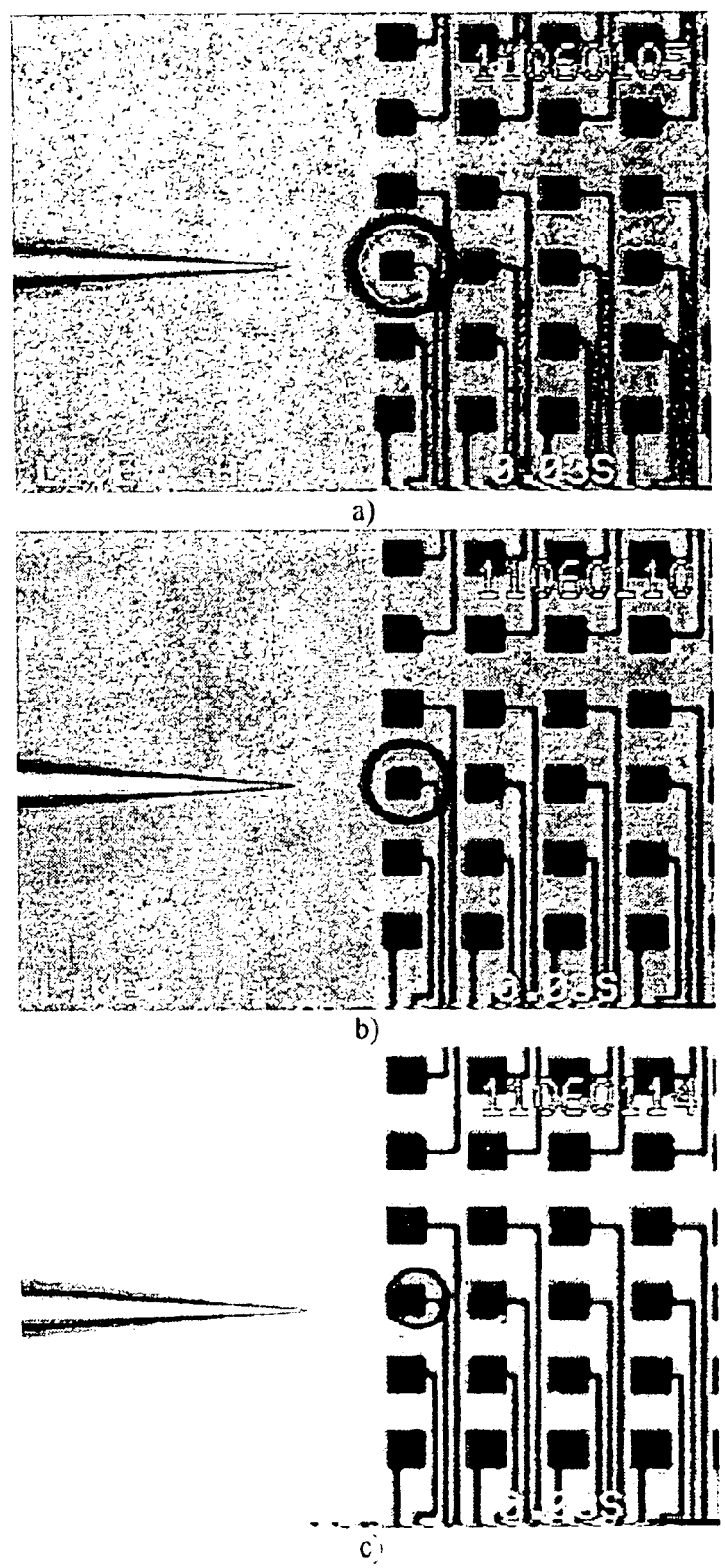
FIG. 16 is a series of photographs of injected droplets showing the variation of diameter as a function of $V_{DEP}$. Injected droplet diameters varied inversely with $V_{DEP}$. These videotape frames show the progressive reduction in droplet diameter for increasing applied $V_{DEP}$ given a fixed injection geometry [a) $V_{DEP}$=120, b) $V_{DEP}$=180, c) $V_{DEP}$=250]. All three frames show a 2.6 μm diameter injector orifice situated 60 μm from an active 30 μm square electrode. The fluid system pressure, P/H, optimized for each applied $V_{DEP}$, was 0.90 for $V_{DEP}$=120, 0.81 for $V_{DEP}$=180, and 0.71 for $V_{DEP}$=250. These droplets correspond to the three data points at Z=2 in FIG. 15.

FIG. 16 is a set of frames captured from videotape showing the progressive reduction in droplet diameter for increasing applied $V_{DEP}$ for the same injection geometry. All three frames show a 2.6 µm diameter injector orifice situated 60 µm from an active 30 µm square electrode.

EXAMPLE 15

Theoretical and Experimental Considerations III

The present disclosure shows that discrete droplet injection by DEP in a no-moving parts manner may be readily achieved and that orifice size, DEP field, electrode-injector spacing, geometry, applied system pressure, and hydrophilic/hydrophobic characteristics of the injector are all significant parameters that may be adjusted to accurately control triggering of injection droplet size, and droplet injection rate.

Specifically, the injector orifice diameter (or, more properly circumference) and the interfacial tension between the injected and suspending media may dictate the static holdoff of the injector. The hydrostatic pressure within the fluid handling system may determine the DEP field necessary to inject droplets and the rate of droplet injection, though not the size of the droplets. Also, the injector-electrode separation, Z, may control injected droplet diameter at low DEP fields.

Figure 17:
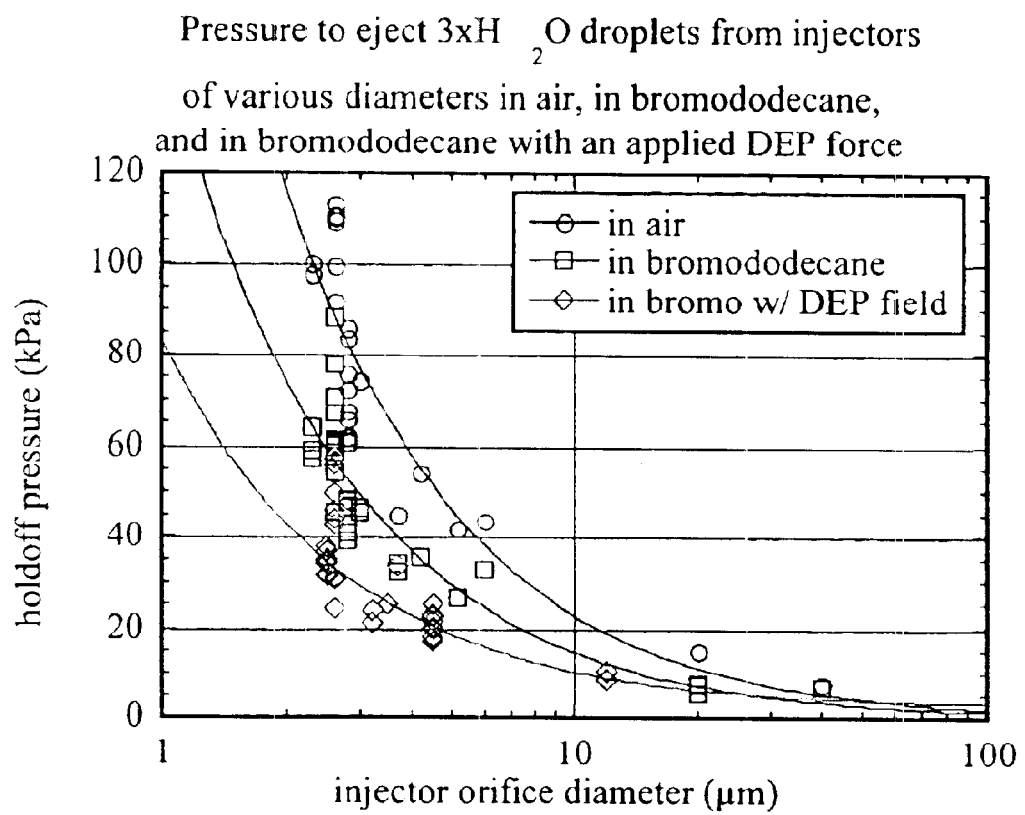
FIG. 17 is a graph illustrating aspects of the present disclosure. It shows holdoff pressure with DEP as a function of injector orifice diameter. It shows measurements of holdoff pressure made with the injector orifice from 2.6 to 40 μm in diameter in open air, and immersed in 1-bromododecane. The two upper curves reflect the differences in interfacial tension of the water/air system (72.0 dyne/cm) (circles), and the water/bromododecane system (52.6 dyne/cm) (squares). The lower curve (diamonds) is fitted to data under various conditions with the DEP field activated in order to illustrate how the DEP field effectively lowers the holdoff of the injector orifice, permitting the injection of discrete droplets below the nominal holdoff pressure.

Turning to FIG. 17, the two upper curves reflect the differences in interfacial tension of a water/air system, and a water/bromododecane system. The water/air interfacial tension is the surface tension for water 72.0 dyne/cm and the calculated water/bromododecane interfacial tension is 52.6 dyne/cm. The lowest curve is fitted to data under various conditions with the DEP field activated in order to illustrate how the DEP field effectively lowers the holdoff of the injector orifice, permitting the injection of discrete droplets below the holdoff pressure.

The upper two curves represent the pressure at which water within the fluid handling system will spontaneously disgorge from an injector orifice of a given diameter. The upper two curves also represent the ability of the injector orifice to act as a check valve for fluid flow. Application of an AC electric field within a dielectric medium permits fluid to be drawn or ejected from the check valve onto the reaction surface.

Summary of Injection Processes

The process of injecting controllable aliquots of aqueous droplets into an immiscible dielectric medium is a function of at least the controllable physical parameters of (1) injector orifice diameter, d, (2) the square of the DEP voltage, $V_{DEP}^2$, (3) fluid system pressure relative to the static holdoff pressure, P/H, (4) injector orifice-electrode edge separation, Z, and (5) electrode lateral length, e.

Figure 18:
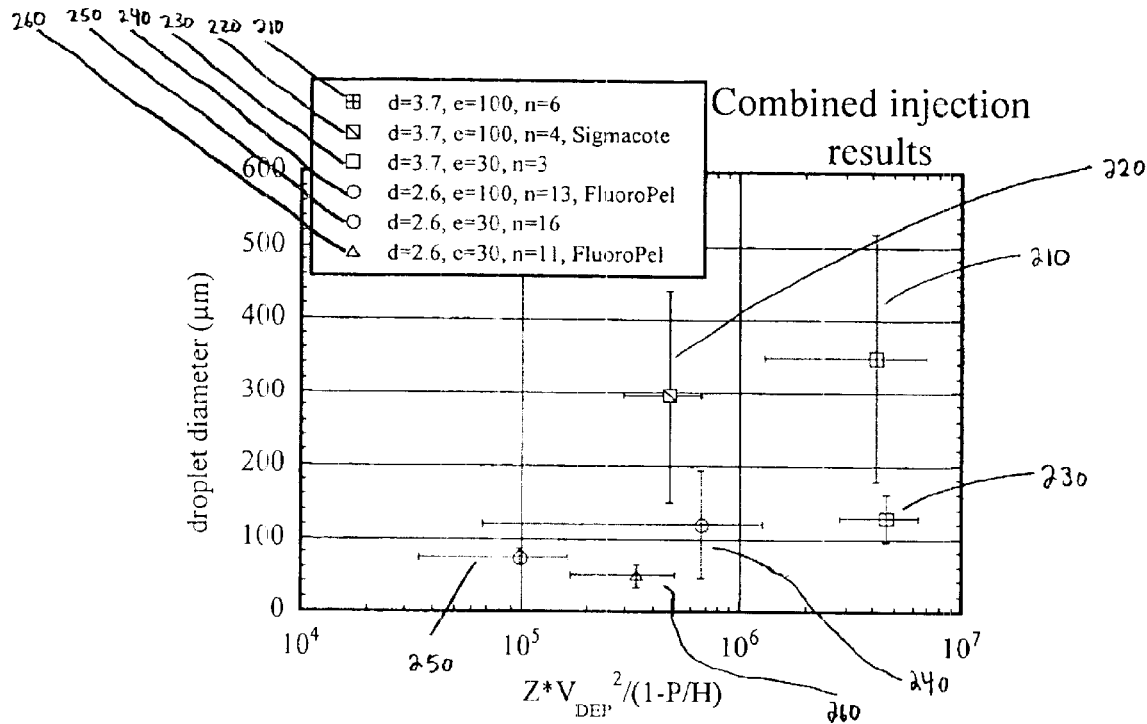
FIG. 18 is a graph illustrating aspects of the present disclosure. It shows mean and standard deviation for combined droplet injection. The means and standard deviations of injected droplets diameters are graphed against a combined function of $V_{DEP}$, P/H, and Z. Changing the interior of the injector orifice from hydrophilic (210) to hydrophobic (220) on the 3.7 μm injector does not change the size of injected droplets, but permits their injection at lower $V_{DEP}$, and P/H. Changing the interior of the injector orifice from hydrophilic (250) to hydrophobic (260) on the 2.6 μm injector permits smaller droplets to be injected rather than drawn, but at higher $V_{DEP}$. Changing the electrode size from 100 μm to 30 μm permits the injection of smaller droplets. In the figure legend, d refers to the injector orifice in μm, e refers to the electrode edge length in μm, and n refers to the number of droplets for the particular data set.

In FIG. 18, the diameter of injected droplets shown on the vertical axis is graphed against a combined function of $V_{DEP}$, P/H, and Z. The individual data points are represented by a mean droplet center-of-mass, and error bars represent the standard deviation in the function for the horizontal axis and the diameter for the vertical axis. The salient features of FIG. 18 include but are not limited to:

1. Changing the interior of the injector orifice from hydrophilic (section 210) to hydrophobic (section 220) on the large 3.7-μm injector does not change the size of injected droplets, but permits their injection at lower $V_{DEP}$, and P/H. This change in hydrophobicity lowered the passive holdoff pressure by only 3%, suggesting that holdoff is almost entirely a function of water/oil interfacial tension and not surface wetting of the injector orifice.
2. Changing the interior of the injector orifice from hydrophilic (section 250) to hydrophobic (section 260) on the small 2.6 μm injector does permit smaller droplets to be injected rather than drawn, though at higher $V_{DEP}$.
3. Changing the electrode size from 100 μm to 30 μm (section 210 vs. section 230, and section 240 vs. section 260) permits the injection of smaller droplets.

The range of injected droplet diameters can be further clarified by normalizing the diameters to the electrode edge length, e, and the electrode/injector separation, Z. Particularly at low $V_{DEP}$ droplets are drawn from the injector orifice until they span the electrode and most of the distance between the electrode and injector. This phenomenon is operationally equivalent to the $V_{DEP}$ temporarily lowering the holdoff pressure, permitting spontaneous injection of fluid onto the reaction surface. If the actual fluid pressure were low enough (P/H<~0.9) the process automatically ceases as soon as the droplet covers the electrode. Further droplets are added unless $V_{DEP}$ is turned off. At higher $V_{DEP}$, smaller droplets are injected, rather than drawn, from the injector.

Figure 19:
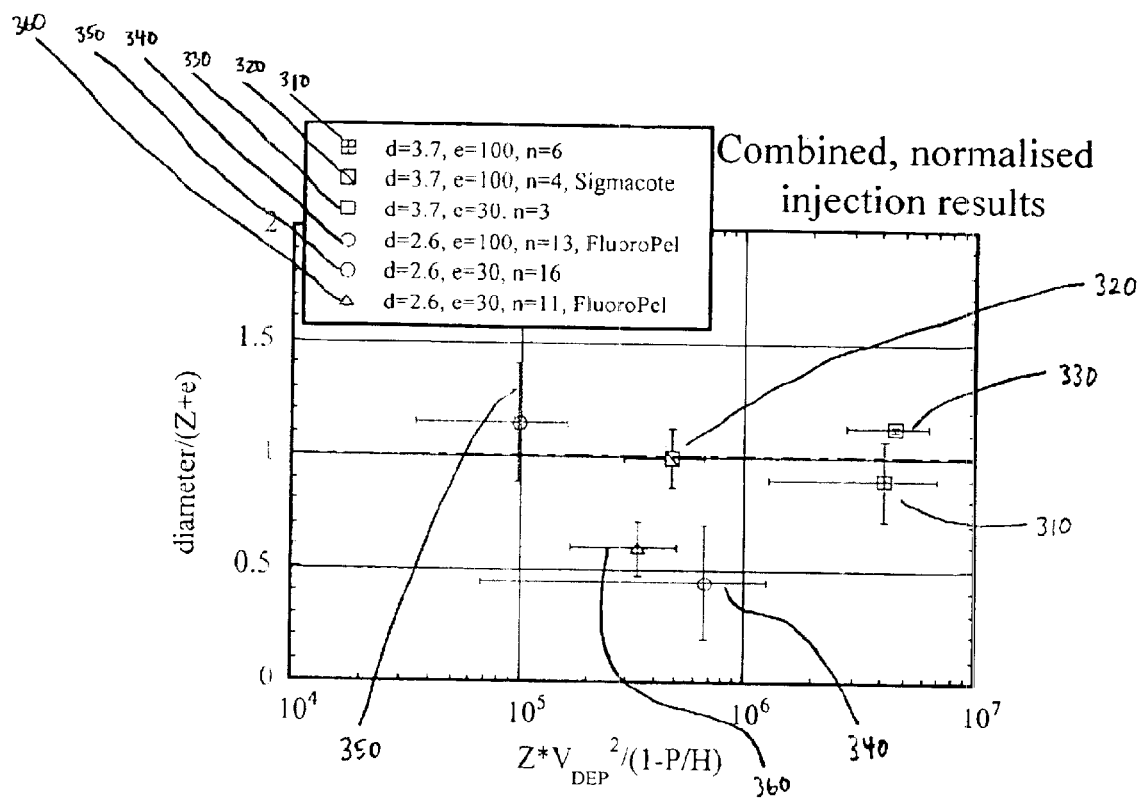
FIG. 19 is a graph illustrating aspects of the present disclosure. It shows combined droplet injection data normalized by injector-electrode distance and electrode size. It graphs the same data as in FIG. 18, but the droplet diameters have been divided by the sum of Z and e. Droplets with diameters dia/(Z+e)>1 (above the dashed line) are drawn and spontaneously injected; droplets with diameters dia/(Z+e)<1 (below the dashed line) are DEP-injected and ejected onto the reaction surface. Injection from larger 3.7 μm injectors is possible only at relatively high $V_{DEP}$. Injection of small droplets is facilitated by having the interior of the injector made hydrophobic. And, injected droplets diameters scale with the electrode dimensions. This implies that the electrode size determines the field gradient relative to the injector. In the figure legend, d refers to the injector orifice in μm, e refers to the electrode edge length in μm, and n refers to the number of droplets for the particular data set.

FIG. 19 graphs the same data as in FIG. 18, but the droplet diameters have been divided by the sum of Z and e, leading to a unit-less quantity. Droplets larger than dia/(Z+e)=1 represent those that are drawn and spontaneously injected. Droplets less than dia/(Z+e)=1 represent those that are DEP-injected and ejected onto the reaction surface. Scaled this way, several things become apparent:

1. Injection from larger injectors, e.g., 3.7 μm is possible only at relatively high $V_{DEP}$.
2. Injection of small droplets is facilitated by having the interior of the injector made hydrophobic (sections 340 and 360 vs. section 350).
3. Injected droplets diameters scale with the electrode dimensions (section 340 and section 360). This implies that the electrode size determines the field gradient relative to the injector.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. Moreover, the different aspects of the disclosed apparatus and methods may be utilized in various combinations and/or independently. Thus the invention is not limited to only those combinations shown herein, but rather may include other combinations.

What is claimed is:

1. A dielectric gate comprising one or more electrodes coupled between an inlet fluid pathway and an outlet fluid pathway, and means for driving the one or more electrodes with AC signals to draw fluid from the inlet fluid pathway to the outlet fluid pathway using dielectrophoretic forces resulting from inhomogeneous electrical fields, wherein the inlet or outlet fluid pathway comprises hydrophilic or hydrophobic surface coatings configured to provide preferential fluid flow directions.

2. The gate of claim 1, wherein the inlet fluid pathway comprises a tube or channel.

3. The gate of claim 1, wherein the outlet fluid pathway comprises a tube or channel.

4. The gate of claim 1, further comprising a chamber covering at least a portion of the gate.

5. The gate of claim 1, further comprising a fluidic injector in operative relation to the inlet fluid pathway.

6. The gate of claim 5, wherein the fluidic injector comprises a hydrophilic or hydrophobic coating.

7. A dielectric gate comprising:
   an inlet fluid pathway;
   one or more electrodes in operative relation with the inlet fluid pathway;
   a hydrophobic patch adjacent at least one of the electrodes;
   an outlet fluid pathway in operative relation with at least one of the electrodes; and
   means for driving the one or more electrodes with AC signals to draw fluid from the inlet fluid pathway to the outlet fluid pathway using dielectrophoretic forces resulting from inhomogeneous electrical fields;
   wherein the hydrophobic patch is configured to inhibit fluid flow from the inlet fluid pathway to the outlet fluid pathway in the absence of the electrical signals.

8. The gate of claim 7, wherein the inlet fluid pathway comprises a tube or channel.

9. The gate of claim 7, wherein the outlet fluid pathway comprises a tube or channel.

10. The gate of claim 7, wherein the inlet fluid pathway comprises hydrophilic or hydrophobic surface coatings defining a virtual channel, which provides preferential fluid flow directions.

11. The gate of claim 7, wherein the outlet fluid pathway comprises hydrophilic or hydrophobic surface coatings defining a virtual channel, which provides preferential fluid flow directions.

12. The gate of claim 7, further comprising a chamber covering at least a portion of the gate.

13. The gate of claim 7, further comprising a fluidic injector in operative relation to the inlet fluid pathway.

14. The gate of claim 13, wherein the fluidic injector comprises a hydrophilic or hydrophobic coating.

15. A system for fluid flow control, comprising:
   a dielectric gate including an inlet and outlet fluid pathway;
   a fluid reservoir coupled to the inlet fluid pathway of the dielectric gate; and
   a fluidic device coupled to the outlet fluid pathway of the dielectric gate; and
   means for driving one or more electrodes with AC signals to draw fluid from the inlet fluid pathway to the outlet fluid pathway using dielectrophoretic forces resulting from inhomogeneous electrical fields.

16. The system of claim 15, wherein the dielectric gate comprises a hydrophobic patch adjacent one or more of the electrodes and configured to inhibit fluid flow from the inlet fluid pathway to the outlet fluid pathway in the absence of the electrical signals.

17. The system of claim 15, wherein the fluid reservoir comprises a pressurized reservoir.

18. The system of claim 15, further comprising an impedance sensor in operative relation to the dielectric gate and configured to count a number of droplets transferred from the inlet fluid pathway to the outlet fluid pathway.

19. The system of claim 15, wherein the system comprises a single chip.

20. The system of claim wherein the fluidic device comprises a capillary electrophoresis device.

21. The system of claim 15, wherein the fluidic device comprises a polymerase chain reaction device.

22. The system of claim 15, wherein the fluidic device comprises a dielectrophoresis field flow fractionation device.

23. The system of claim 15, wherein the fluidic device comprises a programmable fluidic processor.

24. A method for fluid flow control, comprising:

flowing fluid from a fluid reservoir to an inlet fluid pathway;

applying AC signals to one or more electrodes, resulting in inhomogeneous electrical fields, for drawing the fluid from the inlet fluid pathway to an outlet fluid pathway by dielectrophoretic forces arising from a dielectric gate;

flowing the fluid from the outlet fluid pathway to a fluidic device.

25. The method of claim 24, further comprising inhibiting the flow of fluid from the inlet fluid pathway to the outlet fluid pathway using a hydrophobic patch coupled to at least a portion of the dielectric gate.

26. The method of claim 24, further comprising counting a number of droplets transferred from the inlet fluid pathway to outlet fluid pathway using an impedance sensor in operative relation to the dielectric gate.

27. The method of claim 24, wherein flowing fluid from the fluid reservoir to the inlet fluid pathway comprises flowing the fluid through one or more virtual channels defined by hydrophilic or hydrophobic surface coatings, which provide preferential fluid flow directions.

28. The method of claim 24, wherein flowing the fluid from the outlet fluid pathway to the fluidic device comprises flowing the fluid through one or more virtual channels defined by hydrophilic or hydrophobic surface coatings, which provide preferential fluid flow directions.

* * * * *